United States Patent
Clerin et al.

(10) Patent No.: US 7,011,623 B2
(45) Date of Patent: Mar. 14, 2006

(54) EX VIVO REMODELING OF EXCISED BLOOD VESSELS FOR VASCULAR GRAFTS

(75) Inventors: Valerie Clerin, Philadelphia, PA (US); Rebecca Gusic, Philadelphia, PA (US); Keith Gooch, Media, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 307 days.

(21) Appl. No.: 10/165,461

(22) Filed: Jun. 7, 2002

(65) Prior Publication Data

US 2003/0097040 A1 May 22, 2003

Related U.S. Application Data

(60) Provisional application No. 60/297,203, filed on Jun. 8, 2001.

(51) Int. Cl.
 *A61F 2/04* (2006.01)
(52) U.S. Cl. .......................................... 600/36; 623/916
(58) Field of Classification Search ................... 600/36; 606/1, 159, 194; 623/1.1, 903, 916; 435/395, 435/404, 405
See application file for complete search history.

(56) References Cited

U.S. PATENT DOCUMENTS 6,322,553 B1 * 11/2001 Vito .............................. 606/1

OTHER PUBLICATIONS

Conklin, B.S., "Viability of Porcine Common Carotid Arteries i a Novel Organ Culture System," MS Thesis, Georgia Institute of Technology, 1997.*

Berceli, S., et al., "Biomechanics of the venous wall under simulated arterial conditions," *J. Biomech.* 23(10):985-989 (1990).

Bergel, D., "The dynamic elastic properties of the arterial wall," *J. Physiol.* (Lond) 156:458-469 (1961).

Brant, A., et al., "Biomechanics of the arterial wall under simulated flow conditions," *J. Biomechanics* 21(2):107-113 (1988).

Campbell, J.H., et al., "Novel vascular graft grown within recipient's own peritoneal cavity," *Circ. Res.* 85(12):1173-1178 (1999).

(Continued)

*Primary Examiner*—John P. Lacyk
(74) *Attorney, Agent, or Firm*—Evelyn H. McConathy; Drinker Biddle & Reath LLP

(57) ABSTRACT

The present invention provides an ex vivo vascular remodeling methods and system by which an excised, small diameter blood vessel can be harvested and expanded to provide viable vascular grafts, as demonstrated at the physical and molecular levels, and as optimized in vivo. The tissue-engineered vessels generated by the present invention closely resemble native vessels in terms of structure, histologically, including endothelial coverage and intricate structural components such as the internal elastic lamina, viability (as measured with the MTT assay and TUNEL analysis), and function (vasoactivity, mechanical and biomechanical properties). Thus, the resulting vascular grafts behave in a manner similar to native arteries in terms of mechanical integrity, and provide clinically relevant patency rates when implanted in vivo. Moreover, the ex vivo methods and system permit the precise control of the mechanical environment involving the excised vessel, while at the same time permitting careful monitoring of the resulting growth/remodeling, thereby opening new avenues of research regarding the mechanical stimuli responsible for specific aspects of remodeling in vivo.

18 Claims, 14 Drawing Sheets

OTHER PUBLICATIONS

Chesler, N.C., et al., "Transmural pressure induces matrix-degrading activity in porcine arteries ex vivo," *Am. J. Physiol.* 277(5 Pt 2):H2002-2009 (1999).

Chiquet-Ehrismann, R., et al., "The complexity in regulating the expression of tenascins," *Bioessays* 17(10):873-878 (1995).

Cho, et al., "Effects of changes in blood flow rate on cell death and cell proliferation in carotid arteries of immature rabbits," *Circ. Res.* 81(3):328-337 (1997).

Cowan, K.N., et al., "Regression of hypertrophied rat pulmonary arteries in organ culture is associated with suppression of proteolytic activity, inhibition of tenascin-C, and smooth muscle cell apoptosis," *Circ. Res.* 84(10):1223-1233 (1999).

Fitzgibbon, G.M., et al., "Coronary bypass graft fate and patient outcome: angiographic follow-up of 5,065 grafts related to survival and reoperation in 1,388 patients during 25 years," *J. Am. Coll. Cardiol.* 28(3):616-626 (1996).

Fung, Y., *Biomechanics: Circulation.* 2nd ed. (1996).

Fung, Y.C., et al., "Changes of zero-stress state of rat pulmonary arteries in hypoxic hypertension," *J. Appl. Physiol.* 70(6):2455-2470 (1991).

Gessener, U., et al., "Methods of determining the distensibility of blood vessels," *IEEE Trans. Biomed. Eng.* 13:2-10 (1966).

Gooch, K., et al., *Mechanical Forces: Their Effects on Cells and Tissues*, Berlin:Springer, p. 182 (1997).

Gooch, K., et al., "Mechanical Forces Growth Factors in Tissue Engineering," in *Frontiers in Tissue Engineering*, (C. Patrick, A. Mikos, and L. McIntire, Edit.) Pergamon, New York, p. 61-82 (1998).

Gooch, K.J., et al., "Flow- and bradykinin-induced nitric production by endothelial cells in independent of membrane potential," *Am. J. Physiol.* 270(2 Pt 1):C546-51 (1996).

Gooch, K.J., et al., "Exogenous, basal, and flow-induced nitric oxide production and endothelial cell proliferation," *J. Cell Physiol.* 171(3):252-258 (1997).

Herman, I.M., et al., "Hemodynamics and the vascular endothelial cytoskeleton," *J. Cell Biol.* 105(1):291-302 (1987).

Holman, E., "Problems in the dynamics of blood flow, I. Condition controlling collateral circulation in the presence of an arteriovenous fistula following the ligation of an artery," *Surgery* 26:889-917 (1949).

Jones, P.L., et al., "Tenascin-C is induced with progressive pulmonary vascular disease in rats and is functionally related to increased smooth muscle cell proliferation," *Circ. Res.* 79(6):1131-1142 (1996).

Jones, P.L., et al., "Induction of vascular smooth muscle cell tenascin-C gene expression by denatured type I collagen is dependent upon a beta3 integrin-mediated mitogen-activated protein kinase pathway and a 122-base pair promoter element," *J. Cell Sci.* 112(Pt 4):435-445 (1999).

Jones, P.L., et al., "Regulation of tenascin-C, a vascular smooth muscle cell survival factor that interacts with the alpha v beta 3 integrin to promote-epidermal growth factor receptor phosphorylation and growth," *J. Cell Biol.* 139(1): 279-293 (1997).

Kamiya, A., et al., "Adaptive regulation of wall shear stress to flow change in the canine carotid artery," *Am. J. Physiol.* 239(1):H14-21 (1980).

Labadie, R.F., et al., "Pulsatile perfusion system for ex vivo investigation of biochemical pathways in intact vascular tissue," *Am. J. Physiol.* 270(2 Pt 2):H760-768 (1996).

L'Heureux, N., et al., "A completely biological tissue-engineered human blood vessel," *FASEB J.* 12(1):47-56 (1998).

L'Heureux, N., et al., "In vitro construction of a human blood vessel from cultured vascular cells: a morphologic study," *J. Vasc. Surg.* 17(3):499-509 (1993).

Liu, S.Q., "Biomechanical basis of vascular tissue engineering," *Crit. Rev. Biomed. Eng.* 27(1-2):75-148 (1999).

Loftus, I.M., et al., "MMP inhibition reduces intimal hyperplasia in a human vein graft stenosis model," *Ann. N Y Acad. Sci.* 878:547-550 (1999).

Lytle, B.W., et al., "Long-term (5 to 12 years) serial studies of internal mammary artery and saphenous vein coronary bypass grafts," *J. Thorac. Cardiovasc. Surg.* 89(2):248-258 (1985).

Mackie, E.J., "Molecules in focus: tenascin-C," *Int. J. Biochem. Cell Biol.* 29(10):1133-1137 (1997).

Masood, I., et al., "Endothelin-1 is a mediator of intimal hyperplasia in organ culture of human saphenous vein," *Brit. J. Surg.* 84(4):499-503 (1997).

Mavromatis, K., et al., "Early effects of arterial hemodynamic conditions on human saphenous veins perfused ex vivo," *Arterioscler. Thromb. Vasc. Biol.* 20(8): 1889-1895 (2000).

Melkumyants, A.M, et al, "Effect of blood viscocity on arterial flow induced dilator response," *Cardiovasc. Res.* 24(2):165-168 (1990).

Meng, X., K., et al., "Mechanical stretching of human saphenous vein grafts induces expression and activation of matrix-degrading enzymes associated with vascular tissue injury and repair," *Exp. Mol. Pathol.* 66(3):227-237 (1999).

Milnor, W.R., *Hemodynamics*, 2nd ed., Baltimore, Williams & Wilkins, p. 419 (1989).

Mulvihill, D. and S. Harvey, "The mechanism of the development of collateral circulation," *N. Engl. J. Med.* 104:1032 (1931).

Niklason, L.E., et al., "Functional arteries grown in vitro," *Science* 284(5413):489-493 (1999).

Porter, K.E., et al., "Endothelin-B receptors mediate intimal hyperplasia in an organ culture of human saphenous vein," *J. Vasc. Surg.* 28(4):695-701 (1998).

Porter, K.E., et al., "Marimastat inhibits neointimal thickening in a model of human vein graft stenosis," *Brit. J. Surg.* 85(10):1373-1377 (1998).

Porter, K.E., et al., "Production and inhibition of the gelatinolytic matrix metalloproteinases in a human model of vein graft stenosis," *Eur J Vasc Endovasc Surg.* 17(5):404-412 (1999).

Porter, K.E., et al., "The development of an in vitro flow model of human saphenous vein graft intimal hyperplasia," *Cardiovasc. Res.* 31(4):607-614 (1996).

Sandusky, G.E., G.C. Lantz, and S.F. Badylak, "Healing comparison of small intestine submucosa and ePTFE grafts in the canine carotid artery," *J. Surg. Res.* 58(4):415-420 (1995).

Schenk, W., et al., "The regional hemodynamics of chronic experimental arteriovenous fistulas," *Surg. Gynecol. Obstet.* 110:44-50 (1960).

Shinoka, T., et al., "Creation of viable pulmonary artery autografts through tissue engineering," *J. Thorac. Cardiovasc. Surg.* 115(3):536-545 (1998).

Smith, D.J. et al., "Nitric oxide-releasing polymers containing the [N(O)NO]- group," *J. Med. Chem.* 39(5):1148-1156 (1996).

Soyomo, A.A., et al., "Surgical preparation induces injury and promotes smooth muscle cell proliferation in a culture of human saphenous vein," *Cardiovasc. Res.* 27(11):1961-1967 (1993).

Stanley, J., et al., "Fate of 100 aorto-renal vein grafts: characteristics of late graft expansion, aneurysmal dilation and stenosis," *Surgery* 74:931 (1973).

Stansby, G. et al., "Endothelial cell seeding of vascular grafts: status and prospects," *Cardiovasc. Surg.* 2(5):543-548 (1994).

Stansby, G. et al., "Endothelial seeding of compliant polyurethane vascular graft material," *Brit. J. Surg.* 81(9): 1286-1289 (1994).

Stark, G.B., "Rapid elongation of arteries and veins in rats with a tissue expander," *Plastic and Reconstructive Surgery*, 80(4):570-578 (1987).

Tranquillo, R.T., et al., "Magnetically orientated tissue-equivalent tubes: application to a circumferentially orientated media-equivalent," *Biomaterials* 17(3):349-357 (1996).

Uretzky, G. et al., "Long-term evaluation of a new selectively biodegradable vascular graft coated with polyethylene oxide-polylactic acid for right ventricular conduit: An experimental study," *J. Thorac. Cardiovasc. Surg.* 100(5):769-776 (1990).

Vorp, D.A., et al., "Gene expression is altered in perfused arterial segments exposed to cyclic flexure ex vivo," *Ann. Biomed. Eng.* 27(3):366-371 (1999).

Vyalov, et al., "Decreased blood flow rate disrupts endothelial repair in vivo," *Am. J. Path.* 149(6):2107-2118 (1996).

Weinberg, C., et al., "Blood vessel model constructed from collagen and cultured vascular cells," *Science* 231:397-400 (1986).

Wells, S., et al., "In vivo and in vitro mechanical properties of the sheep thoracic aorta in the perinatal period and adulthood," *Am. J. Physiol.* (*Heart Cir. Physiol.*) 274: H1749-H1760 (1998).

Zarins, C.K., et al., "Shear stress regulation of artery lumen diameter in experimental atherogenesis," *J. Vasc. Surg.* 5(3):413-420(1987).

\* cited by examiner

EX VIVO REMODELING OF EXCISED BLOOD VESSELS FOR VASCULAR GRAFTS

REFERENCE TO RELATED APPLICATIONS

This application claims priority to 60/297,203, filed Jun. 8, 2001, herein incorporated in its entirety.

GOVERNMENT INTERESTS

This invention was supported in part by the National Institutes of Health Grant No. R01 HL64388-01A1. The Government may have certain rights in this invention.

FIELD OF THE INVENTION

This invention relates generally to the field of tissue remodeling, specifically the ex vivo remodeling of blood vessels for use as vascular grafts.

BACKGROUND OF THE INVENTION

More than a century ago, based on observations of the microvasculature, Thoma proposed that longitudinal tension controls vessel length. Since then, a number of studies have shown that blood vessels can remodel either physiologically or pathologically when exposed to altered mechanical environments. Arteries exposed to elevated flow (such as arteries upstream of arteriovenous fistulas (Holman, *Surgery* 26:889–917 (1949); Shenk et al., *Surg. Gynecol. Obstet.* 110:44–50 (1960)), collateral arteries carrying flow around an obstruction (Mulvihill, et al., *N. Engl. J. Med.* 104:1032 (1931)), and aortorenal bypass grafts (Stanley, et al., *Surgery* 74:931 (1973)) remodel (autoregulate) to increase their luminal diameter in response to increased flow as the result of vascular smooth muscle cell relaxation. In contrast, arteries experiencing reduced flow decrease luminal diameter.

Animal studies substantiate these clinical observations and suggest that vessels remodel so as to restore the wall shear stress to initial levels (Fung et al., *J. Appl. Physiol.* 70(6):2455–2470 (1991); Kamiya et al., *Am. J. Physiol.* 239(1):H14–21 (1980); Zarins et al., *J. Vasc. Surg.* 5(3): 413–420 (1987)). Inflation of a tissue expander implanted within a rat hind limb over different periods of time ranging from 2 to 21 days increased the length of adjacent blood vessels 83±43%. Relatively slow expansion-induced lengthening (≦10% per day) did not diminish vessel patency, though more rapid expansion did substantially reduced patency (Stark, *Plastic and Reconstructive Surgery*, 30(4): 570–578 (1986)).

However, the complex interdependence between components of the mechanical environment (e.g., pressure, shear, and strain) in vivo has hindered the identification of the specific mechanical stimuli responsible for remodeling. For example, by altering the viscosity of the perfusing medium, Melkumyants and coworkers have reported that by decoupling the effects associated with shear rate, $\partial v_z/\partial r$, (e.g., convection-enhanced transport and streaming potentials) and the wall shear stress, $-\mu \partial v_z/\partial r$, that acute autoregulation is a response to wall shear stress, not to flow rate per se (Melkumyants et al., *Cardiovasc Res.* 24(2):165–168 (1990)). Several widely used systems that expose cultured endothelial and smooth muscle cells to well-defined mechanical environments exist, but extrapolating results from cell culture models to vascular remodeling has proven to be problematic.

Traditional organ culture models employing excised vessels, such as human saphenous veins under static conditions, provide a well-defined chemical/biochemical environment and have been used to study the effects of pre-existing intimal hyperplasia, surgical preparations (Soyomo et al., *Cardiovasc. Res.* 27(11):1961–1967 (1993)), and specific biochemical factors, including bFGF (Soyomo et al., 1993) and ET-1 (Porter et al., *J. Vasc. Surg.* 28(4):695–701 (1998); Masood, et al. *Brit. J. Surg.* 84(4):499–503 (1997) on intimal hyperplasia. The inadequacy of these models is evidenced by the fact that vessels maintained under static conditions, even in the absence of known biochemical atherogenic stimuli, rapidly undergo pathological remodeling, including substantial intimal hyperplasia (Soyomo et al., 1993).

The atherogenic nature of traditional organ culture models appears to be at least partially due to the absence of physiologically relevant levels of mechanical forces. Porter and coworkers developed a crude, first-generation flow system by cutting an excised saphenous vein longitudinally and gluing the adventitial surface of the vein to the inside of a perfused Tygon tube (Porter et al., *Cardiovasc. Res.* 31(4):607–614 (1996)). The application of venous levels of pressure and flow-induced shear stress to excised human saphenous veins partially attenuated intimal hyperplasia associated with traditional organ culture, while arterial levels of pressure and shear stress completely abolished intimal hyperplasia (Porter et al., 1996). These results showed that, with a mechanically active environment, it was possible to maintain blood vessels in organ culture for weeks without pathological changes.

While the mechanical environments used in these studies were intended to mimic aspects of the arterial or venous circulation, they lacked many relevant mechanical features, including temporal variations, cyclic strains, as well as pressure drops across the vessel wall and the resulting transmural flow—each of which is a potentially important mechanical stimulus to blood vessels as summarized in reviews by, e.g., Gooch et al., *Mechanical Forces: Their Effects on Cells and Tissues*, Berlin, Springer, 182 (1997), and by Liu, *Crit. Rev. Biomed. Eng.* 27(1–2):75–148 (1999). Perfusion systems have been developed and used to provide a sophisticated mechanical environment by introducing pulsatile flow, cyclic flexure (Vorp et al., *Ann. Biomed. Eng.* 27(3):366–371 (1999)) and transmural pressure (Chesler et al., *Am. J. Physiol.* 277(5 Pt 2):H2002–2009 (1999)). These have been used to study the effects of the mechanical environment on gene expression (Vorp et al, 1999), endothelial cytoskeleton (Herman et al., *J. Cell Biol.* 105(1): 291–302 (1987), lipid transport across the endothelium (Herman et al, 1987), and vasomotor responses (Labadie et al., *Am. J. Physiol.* 270(2 Pt 2):H760–768 (1996)).

Perfusion systems have also been used to investigate the effect of hydrodynamic forces on endothelial cells, with specific focus on the mechanisms by which endothelial cells perceive a mechanical stimulus and convert it to the initial biochemical response (i.e., mechanotransduction) (Gooch et al., *Am. J. Physiol.* 270(2 Pt 1):C546–51 (1996)), as well as the effect of biochemical pathways stimulated by fluid flow and mechanical forces on cellular proliferation (Gooch et al., *J. Cell Physiol.* 171(3):252–258 (1997); Gooch et al., *Mechanical Forces: Their Effects on Cells and Tissues,* 1997)) and susceptibility to viral infection. In addition, the effect of a hydrodynamic environment on the development of tissue-engineered cartilage has been investigated (Gooch, K., et al., "Mechanical Forces and Growth Factors," in

*Frontiers in Tissue Engineering*, (C. Patrick, A. Mikos, and L. McIntire, editors.) Pergamon, New York. p. 61–82 (1998)).

Vessel cultures have also been used to explore the molecular biology of vascular remodeling, both under static (Porter et al., 1998; Masood et al., 1997; Porter et al., *Brit. J. Surg.* 85(10):1373–1377 (1998); Porter et al., *Eur. J. Vasc. Endovasc. Surg.* 17(5):404–412 (1999)), and mechanically active environments (Chesler et al., 1999; Meng et al., 1999). One area in which the ex vivo vessel models have been particularly insightful is mechanical regulation of matrix metalloproteinases (MMPs), expression and activity (Vorp et al, 1999; Chesler et al., 1999; Meng et al., *Exp. Mol. Pathol.* 66(3):227–237 (1999); Mavromatis et al., *Arterioscler. Thromb. Vasc. Biol.* 20(8): 1889–1895 (2000)), and the role of MMPs in vascular remodeling (Porter et al., 1998; Porter et al., 1999; Loftus et al., *Ann. N Y Acad. Sci.* 878:547–50 (1999)).

Tenascin-C (TN-C) is large (>1000 kDa), disulfide-linked, hexameric extracellular matrix (ECM) glycoprotein that is prominently expressed during embryonic development, epithelial-mesenchymal interactions, wound healing, cancer, and notably, vascular disease (Mackie, *Int. J. Biochem. Cell Bio.* 29(10):1133–1137 (1997)), and is also subject to mechanical regulation. TN-C expression has been shown to be increased in rats and children suffering from pulmonary hypertension (Jones et al., *J. Cell Sci.* 112(Pt 4):435–445 (1999)), and under increased mechanical loading regimes, TN-C expression co-localizes with neointimal lesions expressing epidermal growth factor (EGF) and proliferating cell nuclear antigen (PCNA) (Jones et al., *J. Cell Biol.* 139(1):279–293 (1997); Jones et al., *Circ. Res.* 79(6): 1131–1142 (1996)). The pro-proliferative role of TN-C is supported by in vitro studies that show TN-C acts as a survival factor for cultured smooth muscle cells (Cowan et al., *Circ. Res.* 84(10):1223–1233 (1999)). The majority of studies show that soluble, extracellular, and matrix factors regulate TN-C at the transcriptional level (Chiquet-Ehrismann et al., *Bioessays* 17(10):873–878 (1995)). In addition, targeted suppression of TN-C arrests progressive pulmonary hypertrophy in organ culture (Cowan et al., 1999). Taken together, these data strongly suggest that in the vessel wall the expression of TN-C is regulated by the mechanical environment, and the expression of this protein in turn is a key regulator of SMC proliferation and vascular remodeling.

Nevertheless, there is a sizable unmet demand for effective small-diameter vascular prostheses for use in coronary bypass surgery. Currently, the best replacements for occluded arteries are autologous arteries, which have a cumulative patency rate of 93% after 5 years (Lytle et al., *J. Thorac. Cardiovasc. Surg.* 89(2):248–258 (1985)). However, the number of expendable autologous arteries of appropriate dimensions for bypass grafts is severely limited, although there are numerous expendable arteries of smaller dimensions.

In animal studies where autologous tissue-engineered small-diameter vessels were evaluated in vivo, they performed much worse than an autologous vein would have (e.g., about half of the tissue-engineered vessels had decreased perfusion or loss of patency within 1 month (Niklason et al., *Science* 284(5413):489–493 (1999); Campbell et al., *Circ. Res.* 85(12):1173–1178 (1999)). Donor veins of appropriate dimensions are more readily available and are frequently used, but they have a substantially lower patency. Human saphenous vein grafts have a patency of ~90% at early time points, and 81% after 1 year (Fitzgibbon et al., *J. Am. Coll. Cardiol.* 28(3):616–626 (1996)), but this has been reported to diminish to 45% after 5 years (Lytle et al., 1985).

Thus, the limited availability of suitable autologous arteries, coupled with the poor long-term patency of autologous veins, has led researchers to explore a number of approaches to create small-diameter vascular prostheses. These include using natural (Sandusky et al., *J. Surg. Res.* 58(4):415–420 (1995)) and synthetic polymeric materials (Smith et al., *J. Med. Chem.* 39(5):1148–1156 (1996); Uretzky et al., *J. Thorac. Cardiovasc. Surg.* 100(5):769–776 (1990)), pre-endothelializing existing types of polymer grafts in vitro (Stansby et al., *Cardiovasc. Surg.* 2(5):543–548 (1994); Stansby et al., *Brit. J. Surg.* 81(9):1286–1289 (1994)), and creating bioartificial or tissue-engineered blood vessels from cells and various support structures (Weinberg et al, *Science* 231:397–400 (1986); L'Heureux et al., *J. Vasc. Surg.* 17(3): 499–509 (1993); L'Heureux et al., *FASEB J.* 12(1):47–56 (1998); Tranquillo et al., *Biomaterials* 17(3):349–357 (1996); Niklason et al., 1999; Shinoka et al., *J. Thorac. Cardiovasc. Surg.* 115(3):536–545 (1998)). While there are a number of different approaches to generating autologous tissue-engineered vessels in vitro, they all follow the same general paradigm: isolate specific cell types from blood vessels, expand these cells in vitro, and reassemble these cells into a tissue-engineered blood vessel—with the last step being the major challenge.

Many of these approaches yielded tissue-engineered arteries that grossly resemble native vessels, but in animal studies where tissue-engineered vessels generated in vitro were evaluated in vivo, their performance was inferior to that of autologous veins (Niklason et al., 1999; Campbell et al., 1999; Fitzgibbon et al., 1996). However, it was generally found that the performance of autologous blood vessels (whole vessels) was clearly superior to that of tissue-engineered blood vessels (prepared from only cells derived from the vessels).

There remains, however, a need in the art for a method or system by which a blood vessel can be harvested and used to direct the growth of an intact vessel ex vivo, wherein the newly formed vessel would be of sufficient size to permit the formation of a tissue-engineered vessel, which would be suitable for use as an arterial graft in vivo. Criteria for assessing the remodeled arteries relate both to the extent that the vessels grow ex vivo, and the degree that the remodeled arteries resemble healthy arteries of corresponding dimensions. Even modest increases in vessel dimensions would be potentially useful. Based on rough estimates using Poiseuille's law (i.e., vessels deform iso-volumetrically (Milnor, *Hemodynamics*, $2^{nd}$, 1989)), increasing the internal arterial diameter by 33% will increase the ability of that artery to carry blood by more than 200%. Poiseuille's law, $$Q = -\frac{\pi \Delta P}{8\mu L} \cdot r^4,$$

relates the volumetric flow rate, Q, to the radius of a straight cylindrical tube of radius, r. Increasing the radius from 100% X to 133% X, increases flow from Y to 3.1 Y, a greater than 200% increase in flow.

In addition, in light of the foregoing and because blood vessels in vivo actively remodel (i.e., change size and/or composition) in response to chronic changes in the mechanical environment, the utilization of this ability of intact blood vessels to remodel supports the use of the system and methods of the present invention as a more effective and alternate approach to generating tissue-engineered blood vessels.

SUMMARY OF THE INVENTION

The present invention provides a system and method by which a small blood vessel is harvested with minimal morbidity of the donor, and the diameter, length, and wall thickness of the excised vessel are increased by subjecting the vessel to the appropriate mechanical environment ex vivo over time. Thus, a tissue-engineered vessel is produced, which is suitable for use as a blood vessel graft in vivo.

Clinical observations and animal studies indicate that vessels remodel in response to altered mechanical environments, but the complex interdependence between components of the mechanical environment (e.g., pressure, shear, and strain) in vivo has hindered the identification of the specific mechanical stimuli responsible for specific aspects of remodeling. To identify the mechanical stimuli responsible for vascular remodeling, an ex vivo perfusion system is provided for exposing viable, excised blood vessels, cells and tissues to precisely controlled flow and pressure regimes, while maintaining the viability of the vessel. The excised vessels are housed in a medium-filled chamber, cannulated on each end, and perfused with cell culture medium supplemented with serum and antibiotics (FIG. 1). As in traditional cell or organ culture systems, temperature, pH, $pO_2$, $pCO_2$, and nutrient composition are regulated.

In addition, the system allows for the control of several key aspects of the mechanical environment. It is an advantage of this system over the prior art to offer improved control of the mechanical environment and allow real time monitoring of vessel remodeling. An understanding of which mechanical stimuli control vascular remodeling is utilized to rationally direct the remodeling of vessels ex vivo.

In a preferred embodiment of the invention the ex vivo perfusion system was used to determine which aspects of the mechanical environment direct the remodeling of arteries. Moreover, experimental data have demonstrated the ability to control and measure extravascular pressure in accordance with the provided methods.

Furthermore, based on preliminary data, it appears reasonable to expect increases of vessel length of at least 100%. Unless the length and internal diameter of a vessel are greatly increased, little to no medial thickening maybe required. For example, rough estimates based on Laplace's Law suggest that if the internal diameter of the vessel increase 33%, and thickness of the vessel remains constant, the stresses in the arterial wall will increase a proportional 33%, which is a relatively small increase. This assumes that the wall thickness is small compared to the vessel diameter, and that the average stress across the wall thickness can be estimated with Laplace's equation, which states that the transmural pressure, $p_i - p_o = T(1/r)$. Therefore, the hoop stress, $T/h$, is directly proportional to the radius.

Using carotid arteries as a model system, data is presented demonstrating that mechanically induced, directed remodeling of excised arteries is possible and that the structure and function of the resulting arteries remain comparable to native arteries. At the conclusion of each experiment, vessels were harvested and processed for histology. From histological sections and subsequent immunostaining, indices of vascular remodeling (intimal, medial, and adventitial thickness) and injury (e.g. cellular proliferation, extracellular matrix synthesis by, and phenotypic change of vascular smooth muscle cells, disruption of internal elastic lamina, formation of a neointima, loss of endothelium) were quantified. By subjecting excised porcine arteries to well-defined mechanical environments, it is shown that, in arteries, transmural pressure drop regulates wall thickness, longitudinal tension regulates length, and flow-induced shear stress regulates inner diameter.

Thus, it is an object of this invention to provide a system and method by which small blood vessels, such as arteries, or even veins, can be harvested with minimal donor site morbidity and remodeled ex vivo, thereby engineering blood vessels for autologous small-caliber vascular grafts. In addition, the ex vivo system is advantageously applied to better understand the molecular biology of vascular remodeling by facilitating the testing of hypotheses not amenable to study using in vivo or cell culture models.

It is a further object of this invention to explore the extent to which arteries can be elongated ex vivo, to determine the identity of the mechanical factors that regulate arterial lumenal diameter and wall thickness, and to explore the extent to which the lumenal diameter and wall thickness of arteries can be increased ex vivo. In vivo studies will evaluate the efficacy of arteries elongated ex vivo as autologous arterial graphs in model subjects, to provide data for eventual human application.

It is also an object of the invention to utilize the ex vivo perfusion system to explore the molecular regulation of mechanically induced vascular remodeling by characterizing the expression and regulation of key regulator factors. For example, the spatial expression and distribution of TN-C mRNA and protein resulting from various mechanical loads is monitored in the cultured vessels to determine the region(s) of the TN-C promoter responsible for mechanosensitivity.

Additional objects, advantages and novel features of the invention will be set forth in part in the description, examples and figures which follow, and in part will become apparent to those skilled in the art on examination of the following, or may be learned by practice of the invention.

DESCRIPTION OF THE DRAWINGS

The foregoing summary, as well as the following detailed description of the invention, will be better understood when read in conjunction with the appended drawings. For the purpose of illustrating the invention, there are shown in the drawings, certain embodiment(s) which are presently preferred. It should be understood, however, that the invention is not limited to the precise arrangements and instrumentalities shown.

FIG. 1A is a schematic diagram of an embodiment using only one vessel. FIG. 1B shows an enlargement of the chamber housing the blood vessel 5 from FIG. 1A.

In FIG. 5B, intravascular pressure is shown in the top curve (black line), and extravascular pressure is shown in the middle curve (gray line).

In FIG. 6A, hematoxylin and eosin staining reveal healthy vessel. In FIG. 6B, immunostaining for the smooth muscle cell specific isoform of α-actin strongly stains the media, but not the adventia. In FIG. 6C, immunostaining is specific for proliferating cell nuclear antigen (PCNA). FIG. 6D is a scanning electron micrograph of the luminal face of the vessel. In FIG. 6E, immunostaining of the extracellular matrix protein elastin reveals the internal elastic lamina and underlying striations. In FIG. 6F, terminal dUTP nick-end labeling reveals a very low rate of apoptosis/necrosis.

In FIG. 9A, the effect of adding a KCl solution to the medium bathing the artery is recorded as the time average of the pressure over 1 second. In FIG. 9B, the data shown represents the mechanical testing of a strip cut from an artery on an Instron machine.

DESCRIPTION OF PREFERRED EMBODIMENTS OF THE INVENTION

The invention provides a system and method by which appropriate mechanical environments are applied ex vivo to direct the remodeling of small, excised blood vessels to create tissue-engineered vessels characterized by increased length, internal diameter, and wall thickness. Thus, the small excised vessels, arteries, or even veins, become tissue-engineered blood vessels for use in vascular surgery. The invention further provides an evaluation of the performance of these tissue-engineered blood vessels in vivo.

The disclosed ex vivo system allows investigations of the hypothesis that longitudinal stress or strain induces artery elongation. In addition, while there are autologous donor arteries with proper diameter and wall thickness for vascular grafts, they often are of an insufficient length to meet the required need. For example, the internal thoracic artery has excellent long-term patency, but is of an adequate length for only a single bypass graft. However, recognizing that if the artery could be elongated, it could be used to bypass multiple occlusions, and the use of vessels demonstrating inferior performance could be avoided, the present invention advantageously provides reliable tissue-engineered blood vessels of sufficient length to meet this need. In addition, the ex vivo perfusion system is further used to explore the molecular regulation of mechanically induced vascular remodeling by characterizing the expression and regulation of key regulatory factors, for which the spatial expression and distribution of mRNA and protein are monitored as a result of various mechanical loads.

Thus, the invention provides a protocol by which localized intravascular and extravascular pressures are measured in real time, and the measured pressures are compared with the calculated pressure estimates. In a preferred embodiment of the invention the ex vivo perfusion system was used to determine which aspects of the mechanical environment direct the remodeling of arteries. Moreover, experimental data have demonstrated the ability to control and measure extravascular pressure in accordance with the provided methods.

The Ex Vivo Perfusion System

Figure 1:
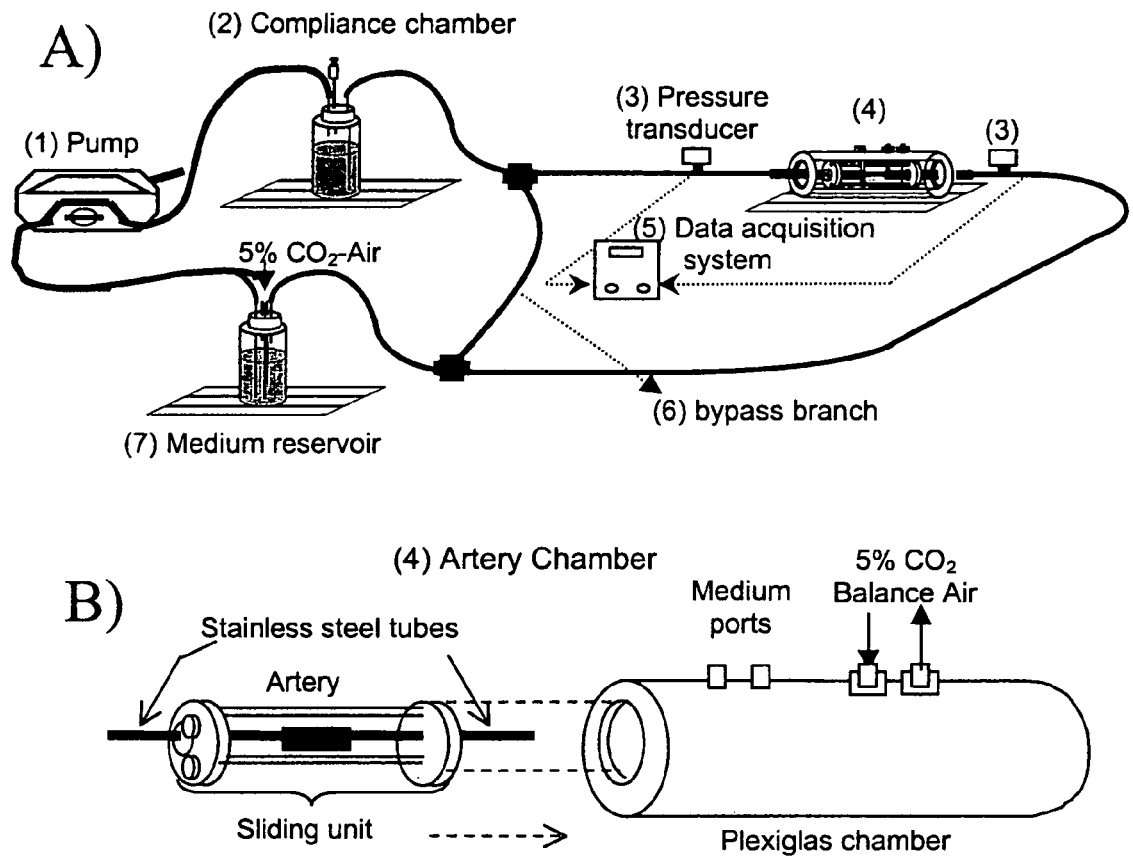
FIGS. 1A and 1B diagrammatically depict the existing ex vivo perfusion system.

The ex vivo perfusion system (FIG. 1A) was designed and built with a capability of independent control specific aspects of the mechanical environment (e.g., the magnitude and time rate of change in intravascular pressure and flow). Turning to FIG. 1A, a Harvard Apparatus pulsatile blood pump 1 pushes fluid clockwise around the circuit. If desired, the initial pulsatile pressure/flow profiles are dampened by the compliance chamber 2, wherein the extent of dampening dependent on the volume of gas present. Pressure in the chamber housing the excised blood vessel 5 is controlled by needle valves 3, which are up and downstream of the chamber. Pressure 4 and flow 6 are measured 250 times per second with in-line probes attached to the corresponding Triton Cardiovascular Measurement Modules (models 200–204 and 200–206) (8 and 9, respectively). Analogue output from these modules is digitized and sent to a personal computer for analysis and storage using LabView.

Medium is pooled in a reservoir 7, which permits gas exchange, before it is returned to the pump. The system is enclosed in a 37° C. environment.

For ease of presentation, only one vessel is shown in the embodiment presented in FIG. 1A. However, multiple vessels can be run in parallel, each having its own housing and, when necessary, corresponding compliance chambers and needle valves.

FIG. 1B provides an enlarged diagram of the chamber housing the blood vessel 5 from FIG. 1A. Vessels are cannulated with two sliding stainless-steel tubes and the entire assembly is inserted into the Plexiglas cylinder. The stainless steel tubes slide independently of the rest of the unit to control the vessel strain. Ports on the Plexiglas cylinder allow the entry and exit of bathing medium and blood gas mixture.

The prototype perfusion system, however, was limited in its ability to control other aspects of the mechanical environment that may be important for vascular remodeling. Therefore, studies were undertaken to expand the capabilities of the system for exposing excised blood vessels to well-defined mechanical environments to enable a) improved control of the mechanical environment and b) real-time monitoring of vascular remodeling. The resulting instrument system has been improved to now enable real-time measurement of pressure and volumetric flow.

Elementary instrumentation principles were employed to interface commercial flow and pressure meters with the PC used for data analysis and storage. Basic fluid mechanics concepts (e.g., those embodied in the Navier-Stoke's equation and Poiseuille equation) were used to guide the design of the existing system capable of independent control of pressure. To ensure that the flow through the vessel is fully developed, the length of straight constant-diameter tubing immediately upstream of the vessel is greater than that calculated for fully developed steady and unsteady flow, 27 cm and 11 cm respectively.

The inlet length for steady flow, $L_s$, (the length required to establish a velocity profile with deviation of less than 1% from parabolic) is given by the equation $L_s=0.16rN_R$, where $N_R$ is the Reynolds number. This relationship holds when $N_R \geq 50$ (Fung, *Biomechanics: Circulation*, 2nd ed. (1996), herein incorporated by reference). $N_R$ for this system is 675, when the Reynolds number is defined as $N_{Re}=\rho rU/\mu$, where $\rho$ is the density of the fluid and $\mu$ is the dynamic viscosity. The viscosity of medium is approximately that of water or about $\frac{1}{5}^{th}$ of that of blood. The average velocity, U, is calculated from $U=Q/\pi r_i^2$.

The unsteady entry length, $L_{us}$, is approximated by the equation, $L_{us}=2.64U/\omega$, where $\omega$ is the pulse rate in radians (Fung, 1996). An understanding of the effects of pulsatility on the velocity profile was aided by considerations of the Womersley number. For example, for the hydrodynamic conditions of the porcine carotid artery, the Womersley Number, $\alpha$, is 1.1.

$$\alpha = 2r(\omega/\nu)^{1/2}$$

where $\omega$ is the pulse rate in radians, r is internal radius of the vessel, and v is the kinematic viscosity (Fung, 1996). The relatively low Womersley number indicates that the transient inertial force is of the same order as the shear force, suggesting that the pulsatile flow can be crudely approximated as a parabolic velocity profile.

Figure 2:
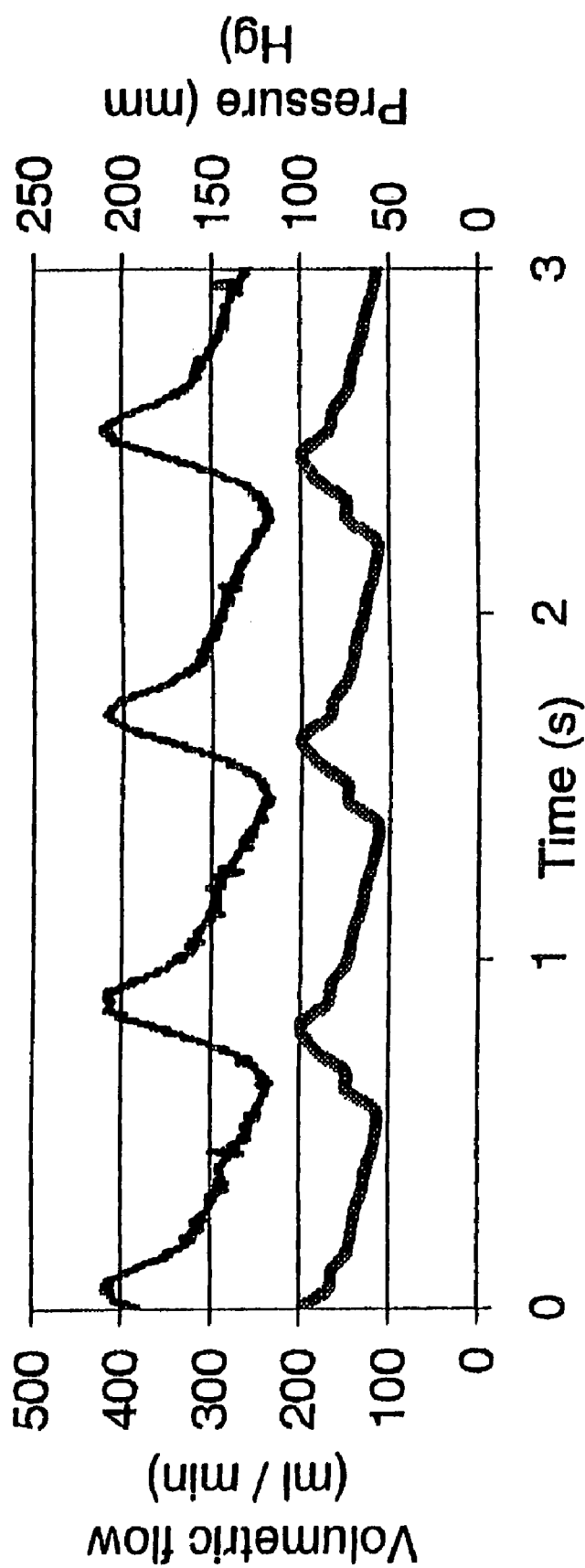
FIG. 2 graphically illustrates volumetric flow rate (upper line) and pressure (lower red line) vs. time for an excised porcine carotid artery exposed to a mechanical environment intended to simulate its native arterial environment. Before harvesting the vessel, the average volumetric flow rate was 320 ml/min as measured using transit-time ultrasound.

The system was validated by running excised vessels (saphenous vein, jugular vein, and carotid artery) in the perfusion system for up to ~10 days. FIG. 2 illustrates representative flow and pressure recordings from an excised porcine carotid artery exposed to a mechanical environment intended to simulate its native arterial environment. Vessels exposed to ex vivo culture were subsequently characterized with immunohistochemistry performed on paraffin sections (FIGS. 4A–4D).

Improved System Offers Enhanced Control of Mechanical Environment

Extravascular pressure: In the embodied perfusion system, the extravascular pressure (i.e., the pressure inside the chamber housing the excised blood vessel) is maintained at 0 mm Hg gauge (i.e., ambient atmospheric pressure) by allowing the chamber to vent to the atmosphere through a 0.22 $\mu$m filter. This situation is an appropriate model of in vivo conditions where extravascular pressure is roughly atmospheric pressure, but it limits investigations into the role of pressures in vascular remodeling. As a result, the perfusion system was modified to allow for control of extravascular pressure: 1) at a given constant level, or 2) to provide constant transmural pressure.

Constant extravascular pressures are provided by attaching to the chamber housing the excised blood vessel a side arm with a fixed height of medium exposed to the atmosphere at the top surface. The extravascular pressure, $P_o$, is estimated from hydrostatics as $P_o = \rho g z$, where $\rho$ is the density of the fluid (1.03 g/cm$^3$), g is the acceleration due to gravity, and z is the height of the column of fluid. The validity of this approach has been demonstrated in preliminary studies, the results of which are shown in FIGS. 4A–4D.

An alternative to maintaining a given extravascular pressure, involves fixing transmural pressure. To do so, the intravascular and extravascular pressures are first set while under no flow conditions (e.g., by using fixed heights of medium exposed to the atmosphere at the top surface). The forces exerted by these two pressures are balanced by the tension generated in the vessel wall. To a first approximation, the circumferential tension generated by the vessel, T, can be calculated from the law of Laplace for thin walls, $T=\Delta Pr$, as the wall thickness h is much less than the vessel diameter, r.

Figure 12:
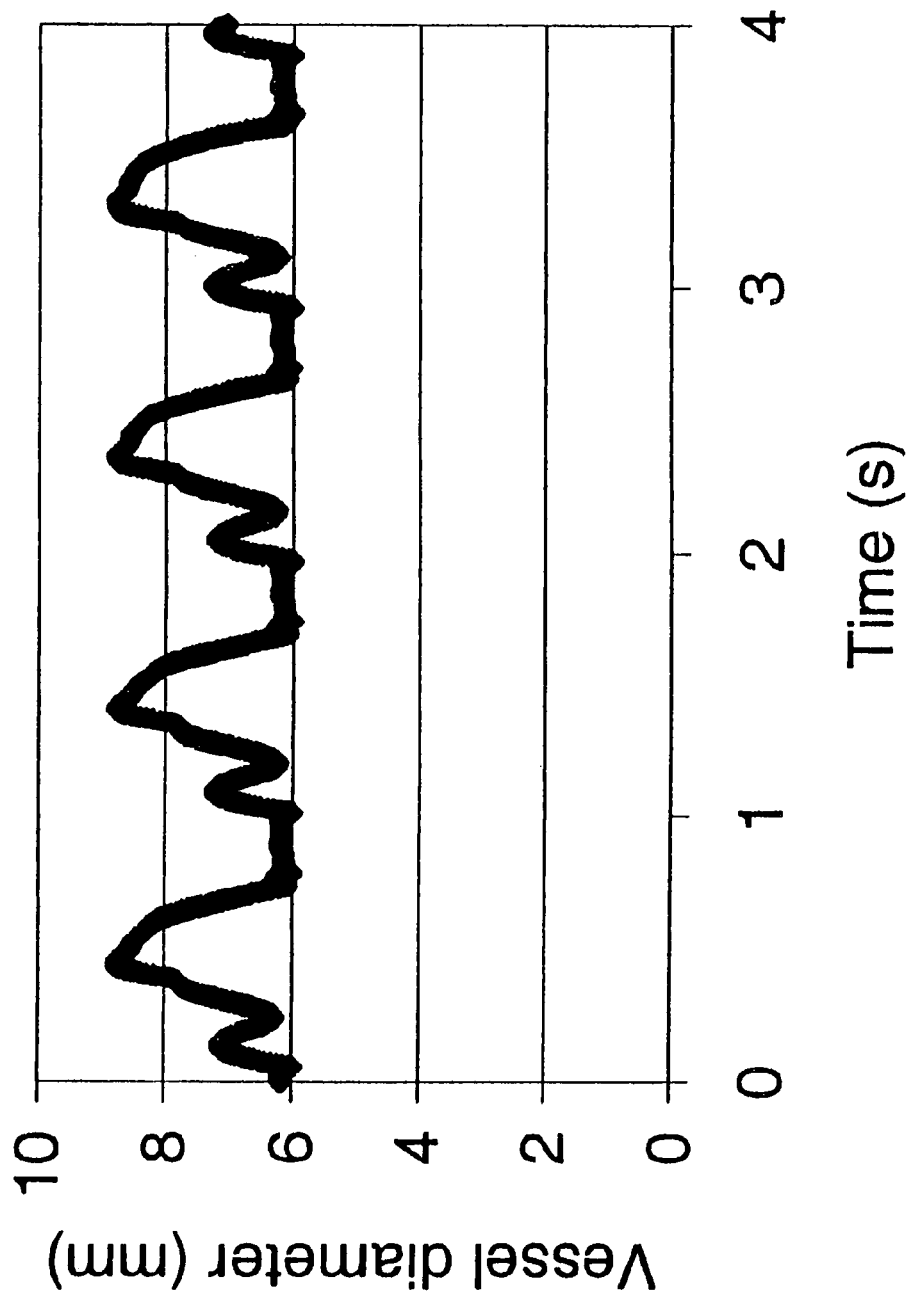
FIG. 12 graphically depicts outer vessel diameter as a function of time of a porcine artery exposed to pulsatile flow.

Radial strain: The outer diameter of the vessels is measured in real time using a laser scanning system (Model # LX2-V10W from Keyence, Woodcliff Lake, N.Y.) (FIG. 12). The embodied system is capable of non-invasively measuring over 250 times per second in vessel diameters up to 1 cm, with a repeatability of 5 $\mu$m. Since the measurement device is external to the perfusion system, with only the scanning laser beam entering, it is easy to relocate the device to measure diameters at different points and in different regions along the vessel (e.g., near the end and at the endpoint). Radial strain, $\epsilon_\theta$, is calculated as $\epsilon_\theta=(D-Do)/Do$, where D is the outer diameter of the blood vessel at a given time and Do is the initial value.

Longitudinal strain: The embodied perfusion system allows for changing the longitudinal strain of the vessel by sliding (extending) the stainless steel tubes on which the vessel is mounted (FIG. 1B). Since the length of the vessel is only being changed very slowly (e.g., in several mm steps once per day), the length is determined by manually measuring the position of the stainless steel tubes entering the vessel chamber. Sonomicrometry is also used to measure the distance between two points on the same side of the outer surface of the vessel. These points will be approximately 2 cm apart, and located along the middle portion of the vessel. From these points, longitudinal strain, $\epsilon_z$, is calculated as $\epsilon_z=(L-Lo)/Lo$, where L is the length of the vessel at a given time, and Lo is the initial length.

The capabilities of the proposed system, wherein the mechanical environment is controlled by the proposed perfusion system device, are summarized in Table 1.

TABLE 1

Key aspects of mechanical environment controlled by perfusion system.

| Mechanical parameter | Magnitude | Time rate of change |
| --- | --- | --- |
| Flow rate (Q) | 0–500 ml/min | Steady to ~3 Hz cycles |
| Pulse rate | | 0–200 beats/min |
| Intravascular pressure ($P_i$) | 0–500 mm Hg | Steady to ~3 Hz cycles |
| Extravascular pressure ($P_o$) | 0–500 mm Hg | Steady or in-phase with intravascular pressure |
| Transmural pressure ($P_i - P_o$) | 0–500 mm Hg | Steady or in-phase with intravascular pressure |
| Longitudinal strain ($\epsilon_z$) | 0 to 100% | Steady to very slow changes (e.g. 10%/day max.) |
| Radial strain ($\epsilon_\theta$) | 0 to 10% | Steady to ~2 Hz cycles |

All pressures are gauge pressures.

Figure 5:
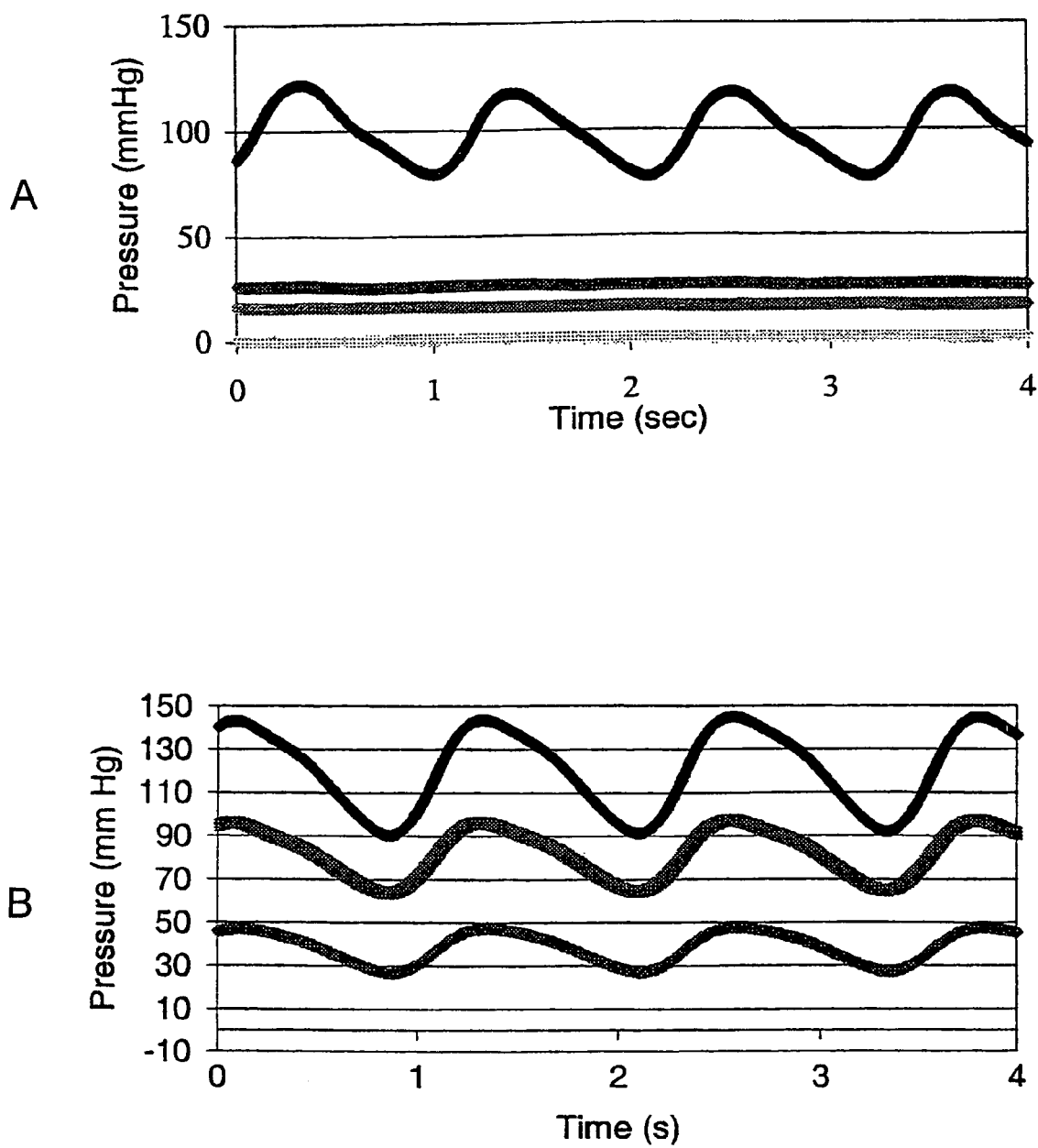
FIGS. 5A and 5B graphically depict as a function of time, the effect of controlling extravascular pressure to atmospheric pressure (FIG. 5A, bottom line, lightest gray), to a fixed amount above atmospheric pressure (FIG. 5A, top two lines, black and dark gray), or such that the calculated transmural pressure is a constant (FIG. 5B, bottom curve).

The extravascular pressure is controlled to atmospheric pressure (FIG. 5A, light gray curve, lowest line), to a fixed amount above atmospheric pressure (FIG. 5A, black and gray curves, remaining lower lines), or such that the transmural pressure is a constant (FIG. 5B, bottom curve).

Next the extravascular compartment is sealed to create a constant volume extravascular system, thus fixing the vessel radius. More precisely, $$\int_0^l \pi r^2\, dr,$$

where l is the length of the vessel, must be a constant volume at any time. The assumption that the vessel radius is fixed at all times is one case, but definitely not the only case that satisfies this integral. The velocity at which the pressure wave travels along the length of the vessel (typically several meters per second) is assumed to be rapid compared to the radial motion of the vessel. However, fixing the radius (and therefore the transmural pressure) for all times is a solution.

The validity of the analysis is confirmed by measuring transmural pressure under the test conditions. Because the pressure drop across the vessel wall depends on the vessel radius and the material properties of the vessel wall, to the extent that neither of these parameters changes, the transmural pressure is regulated. Acknowledging that these assumptions are not trivial, the validity of the conclusions were evaluated by measuring the transmural pressure across ex vivo vessels in real time.

Real-Time Monitoring of Vascular Remodeling

Geometric Remodeling: In the original perfusion system, vascular remodeling could only be assessed at the conclusion of the study when the vessel was fixed and histological sections were prepared, however by the present invention quantification of vascular remodeling has been improved by allowing real-time monitoring of vessel diameter. Although laser-scanning techniques are used to measure radial strain, inner diameter (i.e., lumenal diameter) cannot be measured by this method. Therefore, echo-ultrasound may be used to estimate wall thickness, h. The internal diameter, $D_i$, is calculated as $D_i=D_o-2h$.

Biomechanical Remodeling: Two independent procedures are used to determine the viscoelastic biomechanical properties of the arteries during ex vivo culture: pressure-wave propagation analysis and pressure-diameter analysis (Milnor, *Hemodynamics,* 2nd ed., Baltimore, Williams & Wilkins (1989)). The primary benefit of these two techniques is that they permit continuous real-time evaluation of the mechanical properties of the vessel wall throughout the ex vivo culture period.

"Pressure-wave propagation analysis" compares the pressure harmonics resulting from Fourier transformation of the pressure-vs-time profile generated at several points along the vessel to determine the wave attenuation coefficient, $\alpha$ (which is related to the viscous nature of the vessel) and the true phase velocity, c (which can be used to calculate the dynamic elastic modulus of the vessel). The three-pressure method of wave propagation analysis, which mathematically removes the effects of wave reflection (Gessener et al., *IEEE Trans. Biomed. Eng.* 13:2–10 (1996), herein incorporated by reference), is used, as implemented by others to assess vascular remodeling in vivo (Wells et al., *Am. J. Physiol. (Heart Cir. Physiol.)* 274:H1749–H1760 (1998)).

Consistent with the observations of others, the coefficients rapidly approach zero with increasing harmonic number and truncating the Fourier series at n=10 accurately replicates the observed pressure versus time data and the use of additional terms (e.g., n up to 30) did not noticeably improve accuracy (data not shown).

Figure 13:
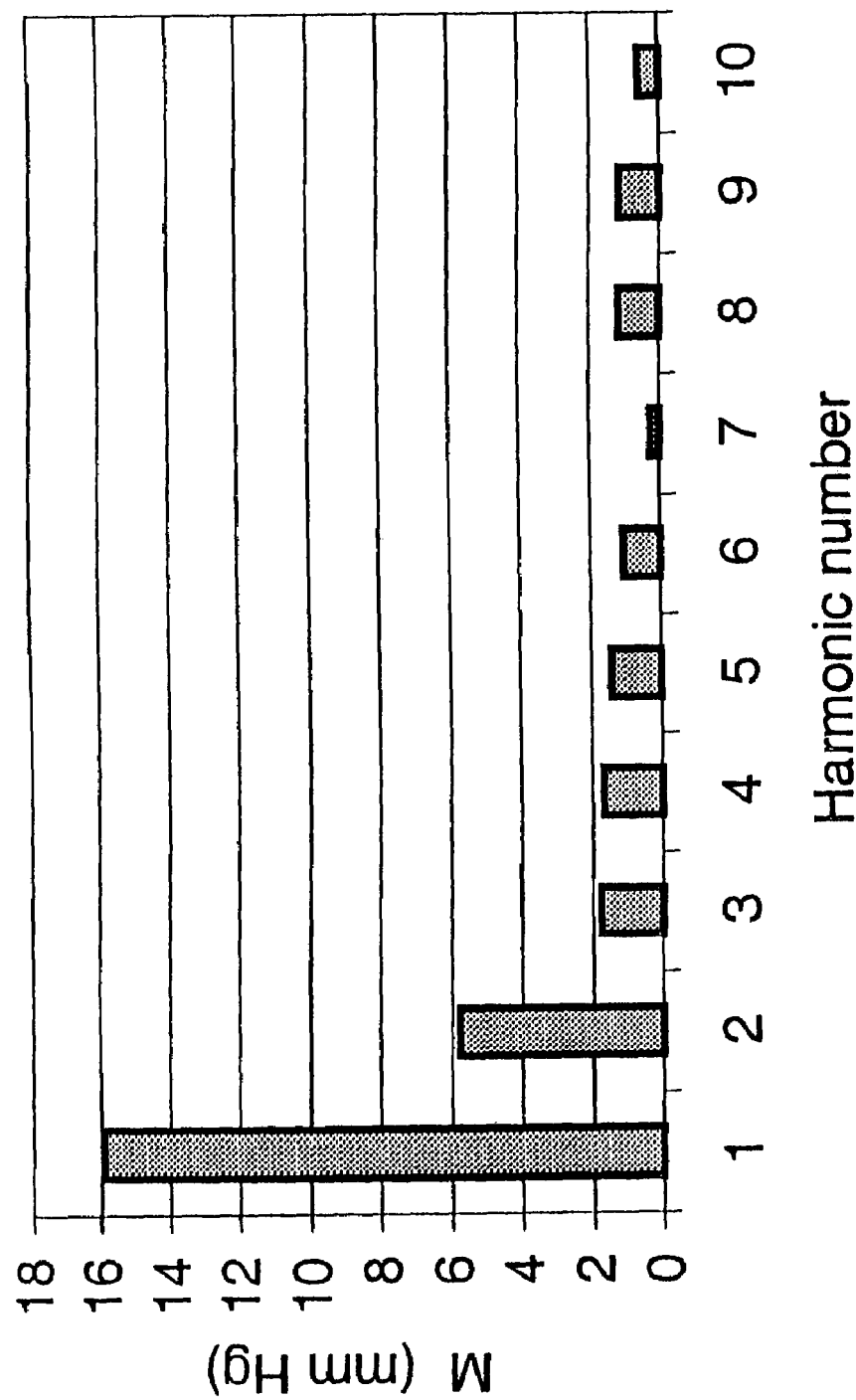
FIG. 13 graphically depicts pressure harmonics for the pressure-vs.-time curve shown in FIG. 2. The pressure harmonics are derived from the coefficients for the Fourier series. Consistent with the observations of others, the coefficients rapidly approach zero with increasing harmonic number; and truncating the Fourier series at n=10 accurately replicates the observed pressure versus time.

P(t) is measured at 3 equally distant points within the vessel using catheter pressure transducers. A Fourier analysis is performed on each pressure profile and the resulting harmonics expressed in complex form (FIG. 13). The coefficients for the Fourier series are as follows:

$$P(t) = a_0 + \sum_{n=1}^{\infty}(a_n \cos(n\pi t/T) + b_n \sin(n\pi t/T))$$

were solved by numerically integrating the integrals $$a_n = \frac{1}{T/2}\int_{-T/2}^{T/2} P(t)\cos(n\pi t/T)dt \text{ for } n = 0, 1, 2, \ldots \text{ and}$$

$$b_n = \frac{1}{T/2}\int_{-T/2}^{T/2} P(t)\sin(n\pi t/T)dt \text{ for } n = 1, 2, 3\ldots$$

The pressure harmonic, $\Delta P$, and the phase angle, $\phi$, were then obtained using the relationships $M=\sqrt{a^2+b^2}$ and $\phi=\arctan(b/a)$. Alternatively P(t) can be expressed as a complex number in the form $$P(t) = \frac{A_0}{2} + \frac{1}{2}\sum_{n=1}^{\infty}(A_n - jB_n)e^{jn\omega t} + \frac{1}{2}\sum_{n=1}^{\infty}(A_n = jB_n)e^{-jn\omega t}.$$

Thus, the resulting harmonics are substituted into Bergel's equation for the true wave propagation coefficient, $$\gamma = \frac{1}{\Delta x}\cosh^{-1}\left(\frac{P_1 + P_3}{2P_2}\right)$$

The true wave propagation coefficient describes the transmission characteristics of each pressure harmonic as it travels through an artery. It consists of a real portion, which is the attenuation coefficient a, and an imaginary portion, which is the angular frequency divided by the true phase velocity, c (i.e., $\gamma=a+(\omega/c)$. The dynamic elastic modulus, $E_{dyn}$, is related to true phase velocity by the equation $E^{dyn}=3\rho r_o/(h(2-h/r_o))c^2$ where $\rho$ is the density of the cell culture medium, h is the arterial wall thickness, and $r_o$ is the external diameter.

In addition, "pressure-diameter transient analysis" harmonics resulting from Fourier transformation of the pressure and external radius transients over the pulse cycle is used to calculate the complex viscoelastic modulus (E*) using the equation of Bergel (*J. Physiol.* (Lond) 156:458–469 (1961)), which is herein incorporated by reference, $$E^* = \left[\frac{3r_i^2 r_o}{2(r_o^2 - r_i^2)} \cdot \frac{M}{\Delta r_o}\right] \cdot e^{(j\theta)}$$

where $r_i$ and $r_o$ are the internal and external radii, respectively, M is the amplitude of the pressure harmonic, $\Delta r_o$ is the amplitude of the radius harmonic, $\theta$ is the phase angle between the corresponding pressure and radius harmonics, and j is $\sqrt{-1}$. As a test for internal consistency, the real component E* from the pressure-diameter transient analysis is compared to the dynamic elastic modulus, $E_{dyn}$, obtained form the pressure wave propagation analysis.

Figure 9:
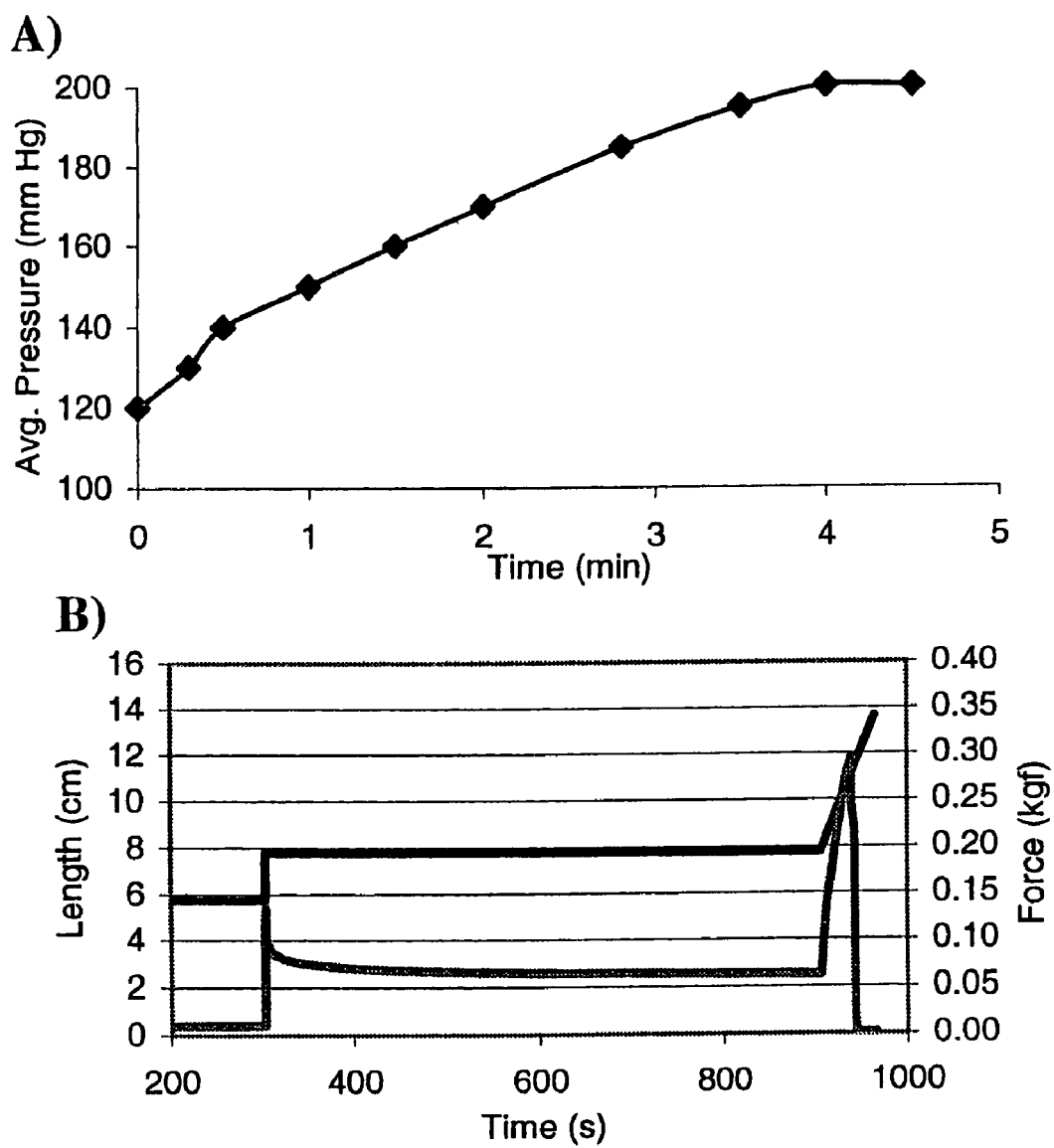
FIGS. 9A and 9B graphically depict an assessment of arterial function of porcine carotid arteries cultured for 9 days ex vivo.

To further assess the accuracy of the real-time measurements of mechanical properties performed while vessels are in the ex vivo perfusion system, static and dynamic stress-strain relationships are measured from axial and longitudinal strips prepared from select vessels. The static and dynamic stress-strain measurements are made on, e.g., a fully digital Instron machine (model 5543) with a positional accuracy of 0.156 $\mu$m (FIG. 9B).

In addition to facilitating the determination of the applied forces that modulate remodeling (e.g., absolute pressure or transmural pressure), the ex vivo perfusion system provides insight into the actual stresses to which the vessels actually respond. By measuring the acute variations in vessel diameter in response to cyclic changes in measured transmural pressure, it is possible to estimate some of the stresses in the vessel wall. Following the Berceli analysis of the biomechanics of excised arteries (Brant et al., *J. Biomechanics* 21(2):107–113 (1988)) and veins (Berceli et al., *J. Biomech.* 23(10):985–989 (1990)) (each of which are incorporated by reference) exposed to various hemodynamic conditions, the axial stress ($T_{zz}$) and hoop stress ($T_{\theta\theta}$) are estimated.

Each of these parameters can be expressed as functions of the incremental modulus ($E_{inc}$), essentially the real component of the complex viscoelastic modulus applied over a limited range of strain. This is calculated as follows:

$$E_{inc} = \frac{TP_{max} - TP_{min}}{r_{o,max} - r_{o,min}} \cdot \frac{2(1-\sigma^2)r_{i,avg}^2 r_{o,avg}}{r_{o,avg}^2 - r_{i,avg}^2};$$

$$T_{zz} = \frac{\sigma E_{inc}}{(1-\sigma^2)} \cdot \frac{\eta}{r_{i,min}};$$

$$T_{\theta\theta} = \frac{E_{inc}}{(1-\sigma^2)} \cdot \frac{\eta}{r_{i,min}} + \frac{E_{inc}h^2\eta}{12r_{i,min}^3(1-\sigma^2)}$$

where TP is transmural pressure, r is radius, $\mu$ is dynamic fluid viscosity, h is wall thickness, and $\eta$ is the measured displacement of the vessel wall, and the subscripts min, max, and avg refer to the minimal (diastolic) value, the maximal (systolic) value, and average values, respectively.

To a very close approximation, Poisson's ratio, $\sigma$, is 0.5 for blood vessels (i.e., vessels deform iso-volumetrically). In this case, the vessel wall is considered elastic, axisymmetric, semi-infinite in length, straight with circular cross-section, constrained from motion longitudinally and the radial displacement is small compared to the radius. These calculations provide estimates of the mechanical stresses in the vessel wall and the incremental modulus aid in the quantification of remodeling. The calculated mechanical stresses are correlated with the observed vascular remodeling.

EXAMPLES

The invention is further described by example. The examples, however, are provided for purposes of illustration to those skilled in the art, and are not intended to be limiting. Moreover, the examples are not to be construed as limiting the scope of the appended claims. Thus, the invention should in no way be construed as being limited to the following examples, but rather, should be construed to encompass any and all variations which become evident as a result of the teaching provided herein.

Although the disclosed experiments were conducted using porcine vessels as models to allow for the detailed in vivo evaluation of the tissue-engineered vessels, the findings are directly applicable to human vascular replacement and provide the foundation for human tissue studies.

For all experiments, vessels were harvested from anesthetized pigs prior to euthanization. Using aseptic technique, an incision were made, the vessel were separated from surrounding fascia and connective tissue, and the vessel was excised. The vessel was briefly washed in buffer and submerged in cell culture medium until placed in the perfusion system no more than 2 hours later. Unless stated otherwise, the duration of each experiment was 4 weeks, which has been shown to be an adequate amount of time to observe substantial vascular remodeling in vivo.

Example 1

The Perfusion System: Control of Mechanical Environment

The perfusion system consisted of a peristaltic pump, compliance chamber, artery chamber, and reservoir, all connected using Tygon laboratory tubing (Formula R-3603, Fisher Scientific, Pittsburgh, Pa.), ports for injection into or sampling from the perfusing medium, and pressure transducers (Model MER100, Triton Technology, Inc., San Diego, Calif.) upstream and downstream from the artery (FIG. 1A and 1B). Steady flow was provided by a Masterflex roller pump (1) (Model 7553-70, Cole-Parmer, Vernon Hills, Ill.) with Masterflex Tygon LFL pump tubing (Formula 06429-25, Fisher Scientific, Pittsburgh, Pa.). Real-time pressure data were acquired via an analog-digital board (Model PCI-6023E, National Instruments, Austin, Tex.) connected to a Triton System 6 Twinpak Chassis (Active Redirection Transit-Time Flow Module, Model 200-206 and Dual Pressure Amplifier Module, Model 200-204, Triton, San Diego, Calif.). Data were visualized and recorded using a LabView-based routine (LabView Full Development System, National Instruments, Austin, Tex.) on a PC. Gas exchange was provided to both the artery chamber and reservoir via 5% $CO_2$ bubbling chambers. The entire system, except for the roller pump, was maintained in a dark, 37° C. environment. All components were sterilized using ethylene oxide and assembled under sterile conditions.

The pulsatile-flow pump forces medium through the ex vivo perfusion system with a well-defined volumetric flow rate. Controlling the compliance and the resistance of the system allows for a wide range of mechanical environments (with respect to magnitude and time rate of change) ranging from arterial to venous conditions as well as supra- and sub-physiological conditions. As shown in FIG. 2, the measured ex vivo pressure (lower line) and volumetric flow profiles (upper line) are maintained in a mechanical environment at values that simulate typical conditions of a porcine carotid artery in vivo. Typical hemodynamic values for pigs are a pulse of ~80 beats per minute and arterial blood pressure ~100/60 mm Hg. Before harvesting the vessel, the average volumetric flow rate was 320 ml/min as measured using transit-time ultrasound. In addition to replicating in vivo pressure and flow profile qualitatively, specific quantitative features were also accurately reproduced (FIG. 2).

Table 2 summarizes key aspects of the mechanical environment controlled by the existing perfusion system and the ranges over which these parameters can be controlled.

TABLE 2

| Mechanical parameter | Magnitude | Time rate of change |
|---|---|---|
| Flow rate | 0–500 ml/min | Steady to ~3 Hz |
| Intravascular pressure | 0–500 mm Hg | Steady to ~3 Hz |
| Pulse rate | | 0–200 beats/min |
| Pulse pressure | 0–500 mm Hg | Steady to ~3 Hz |
| Extravascular pressure | 0 mm Hg | Steady |
| Longitudinal strain | 0 to 100% | Steady to ~10%/day |

Note that while some of these parameters are independent of one another (e.g., average intravascular pressure and average flow can be independently controlled), other parameters are coupled (temporal variations in pressure and flow are linked). Though it would be ideal to have independent control of each mechanical parameter, this is not always feasible. For example, radial strain is dependent on parameters that can be directly controlled (e.g., intravascular and extravascular pressure), as well as other parameters that cannot be directly controlled (e.g., wall thickness and mechanical properties of the vessel, such as modulus). Therefore, given the number of degrees of freedom in the system, it is not possible to arbitrarily set Pi, Po and $\epsilon_\theta$.

Example 2

Determining which Mechanical Factors Regulate Remodeling of Arteries

Artery Harvest, Preparation and Maintenance: Carotid arteries from neonatal (~5-kg) and juvenile (~30-kg) pigs were harvested by cardiothoracic surgeons at the Children's Hospital of Philadelphia after the animals were euthanized. Carotid arteries from adult pigs (~100-kg) were obtained from freshly exsanguinated pigs at a local abattoir. Arteries were transported in ice-cold culture medium (Dulbecco's Modified Eagle's Medium (DMEM) supplemented with 10% fetal bovine serum, 100 U/mL penicillin and 100 µg/mL streptomycin, all from Life Technologies, Inc., Rockville, Md.). Upon arrival, arteries were prepared within a laminar flow hood using sterile instruments.

Arteries, measuring 3–6 cm in length, were individually cleaned of excess adventitial and connective tissue. Sections were taken for histology, methylthiazol tetrazolium (MTT) assay and, in some cases, dry weight and/or mechanical testing. Dry weight measurements were made after at least 8 hours in a Speedvac system (SC100, Thermo-Savant, Holbrook, N.Y.).

Arteries were individually installed into the artery chamber and pressurized with medium to locate leaks. Installation consisted of cannulating the artery onto ribbed stainless steel rods (stainless steel 8, 10 or 13 gauge microtubing, McMaster-Carr, Dayton, N.J.) via silk sutures, where the outer diameter of the rod roughly matched the inner diameter of the artery. Whole, leak-free artery segments were installed at the approximated in vivo length prior to perfusion (initial ex vivo loaded length) unless stated otherwise. The initial extension ratio (ex vivo loaded to unloaded length) was determined for each artery from neonatal and juvenile animals by measuring the length of the artery before and after harvest (unloaded). For arteries from adult animals where in vivo length was not measurable, a ratio of 1.5 was used, since the average ratio from neonatal and juvenile arteries was 1.47±0.03.

After installation of the artery, the chamber was filled with ~200 mL of 37° C. culture medium, completely submerging the artery. The chamber was then connected to the perfusion system containing ~500 mL of 37° C. culture medium, wherein the desired volumetric flow rate had been previously established (10–15 mL/min). Steady flow was then diverted to the artery chamber from the bypass branch.

Carotid Arteries from Neonatal Pigs: Five carotid arteries obtained from neonatal pigs were installed in the ex vivo perfusion system at their physiological loaded length and elongated $\frac{1}{6}^{th}$ of the initial loaded length (16.7%/day) on days 2 to 7 of a 9 experiment. Control arteries from neonatal pigs were cultured under identical conditions at fixed length (n=6, separate study by (Clerin et al., *Ann. Biomed. Eng.* 29(suppl):S-145 (2001)). All arteries were perfused at the approximated in vivo volumetric flow rate of 50 ml/min.

For the higher volumetric flow rates (50 mL/min, arteries from neonatal pigs) the flow rate was increased slowly over a 2-hour period until the desired flow rate was achieved. The flow rate for neonatal arteries was chosen to approximate the in vivo flow rate for neonatal carotid arteries, however subsequent studies determined that subphysiological flow rates were necessary to abrogate de-endothelialization and massive cell death in neonatal arteries (Clerin et al., 2001).

Figure 3:
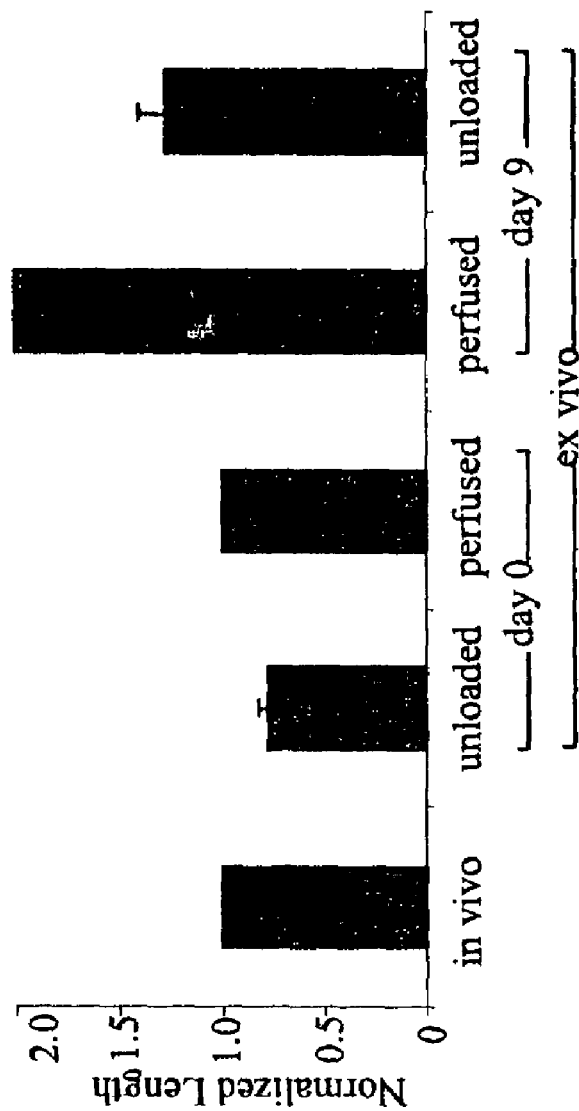
FIG. 3 graphically compares artery length for neonatal elongation experiments (n=5). Each artery length was normalized by individual ex vivo unloaded length (i.e., all arteries unloaded lengths are 1 on day 0); average data are shown with SEM. (**) indicates $p<0.005$.
Figure 4:
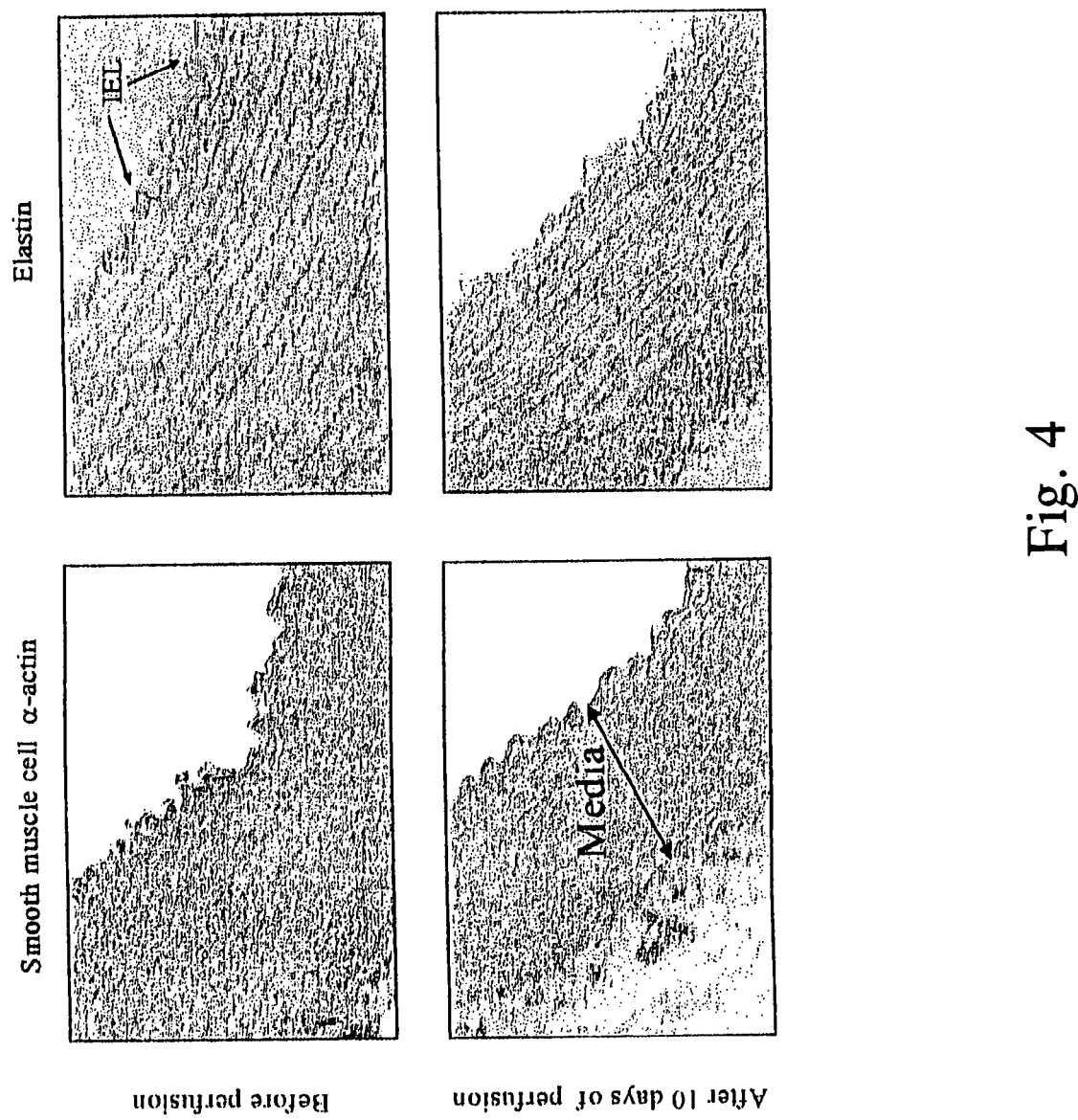
FIGS. 4A–4D photographically depict the immunohistochemistry of paraffin sections prepared from porcine carotid arteries before (FIGS. 4A and 4B) and after (FIGS. 4C and 4D) 10 days of perfusion. Staining for smooth muscle α actin (FIGS. 4A and 4C) and for elastin (FIGS. 4B and 4D) allows identification of the internal elastic lamina (IEL) and the media, both of which are important landmarks used to quantify vascular remodeling.

Upon removal from the perfusion system, control arteries retained no increase in unloaded length, while elongated arteries retained a 65.2±4.5% increase in unloaded length (FIG. 3). Under these flow conditions, histological evaluation revealed that both elongated and control arteries were denuded of their endothelial cells, had lost most of their cellularity, especially in the inner medial region, and had high levels of cell death. The average MTT index was 0.35±0.13 (n=5) demonstrating low viability as compared to control arteries which measured 0.87±0.26 (n=6, p=0.06).

Carotid Arteries from Juvenile Pigs: Because of these findings, the flow rate for juvenile and adult arteries were both chosen to be 10–15 mL/min, 5–10% of the approximated in vivo flow rates for each artery. The artery chamber was maintained at atmospheric pressure by venting the chamber to the atmosphere via a 0.22-$\mu$m filter. The average time from harvest to installation in the perfusion system was 60–90 minutes for neonatal and juvenile and 2–3 hours for adult arteries.

A total of 18 carotid arteries from juvenile pigs were perfused in the ex vivo perfusion system and either elongated (n=12, "elongated arteries") or held at physiological loaded length (n=6, "control arteries") for 9 days (Table 3). All juvenile arteries were installed at their physiological loaded length and perfused at a volumetric flow rate of 10–15 ml/min, previously shown to be within the optimum range for retaining artery viability (Clerin et al., 2001).

trend (8.5±13.7%, n=3). Viability of all arteries, as assessed by MTT index, was similar to fresh arteries.

Application of Longitudinal Strain (Elongation Protocol): In preliminary studies, it was demonstrated that by applying a longitudinal strain, vessels could be elongated ~100% over 9 days. Longitudinal strain was applied daily to the artery by manual displacement of the steel rods. Arteries perfused for 9 days were held at their physiological length (initial loaded length) on day 1, stretched at a rate of $\frac{1}{6}^{th}$ or $\frac{1}{12}^{th}$ of the physiological length per day from day 2 to 7, held at the final stretched length on day 8, and excised on day 9. Similarly, arteries perfused for 27 days were held at constant length (initial loaded or unloaded length) on days 1 to 3, stretched $\frac{1}{20}^{th}$ of the installed length on days 4 to 23, held at the final stretched length on days 24 to 26, and excised on day 27. Control arteries were cultured in the perfusion system under identical conditions, but were held at their physiological length (initial loaded length).

The in vivo length of the porcine arteries were noted prior to excision. The length of the arteries without an applied load were measured and the vessels were placed in the perfusion system at their in vivo lengths. Vessels were randomly assigned to two groups. Vessels in the first group (control) were arteries were cultured in the perfusion system

TABLE 3

Summary of ex vivo culture experiments.

| Age of Donor Pigs | Volumetric Flow Rate (ml/min) | Longitudinal Strain Protocol | n | Length increase | Rupture |
|---|---|---|---|---|---|
| Neonatal | 50 | 100% increase in physiological loaded length in 9 days (16.7% on days 2 to 7) | 5 | 5** | 0 |
| Juvenile | 10–15 | Fixed physiological loaded length, 9 days | 6 | 0 | 0 |
|  | 15 | 50% increase in physiological loaded length in 9 days (8.3% on days 2 to 7) | 8 | 6** | 2 |
|  | 15 | 66% increase in physiological loaded length in 7 days (13.2% on days 2 to 6) | 1 | 0 | 1 |
|  | 15 | 100% increase in physiological loaded length in 9 days (16.7% on days 2 to 7) | 3 | 0 | 3 |
| Adult | 10 | 100% increase in physiological unloaded length in 7 days (16.7% on days 2 to 7) | 1 | 0 | 0 |
|  | 10 | 100% increase in physiological unloaded length in 27 days (5% on days 4 to 23) | 2 | 0 | 0 |
|  | 10 | 100% increase in physiological loaded length in 9 days (16.7% on days 2 to 7) | 1 | 0 | 1 |
|  | 10 | 100% increase in physiological loaded length in 27 days (5% on days 4 to 23) | 2 | 0 | 2 |

A significant increase in unloaded length (p < 0.005) is denoted by**.

Carotid Arteries from Adult Pigs: All carotid arteries from adult pigs were subjected to rapid protocols (stretched 16.7% on days 2 to 7 of a 9 day experiment, n=1) or slow stretching protocols (stretched 5% on days 4 to 23 of a 27 day experiment, n=3), ruptured prior to completion on days 6, 15 (n=2), and 19 (Table 3). Rupture was avoided by installing arteries at ex vivo unloaded length, and elongating 5% of the unloaded length on days 4 to 23 of a 27-day experiment (n=2), or elongating 16.7% of the unloaded length on days 2 to 7 of a 9-day experiment (n=1, removed on day 7 due to suture failure).

None of the arteries retained an unloaded length increase upon removal from the perfusion system. Arteries installed at unloaded length all increased their wet weight (41.6±1.7%, n=3) while those that ruptured showed no clear under identical conditions, but were held at their physiological length (initial loaded length). Vessels in the second group were subjected to different longitudinal strain rates (~2 to 20% per day) for the various indicated durations (1 week to 2 months). At the end of the experiment, the lengths of the vessels without applied loads were measured and compared. All unloaded lengths reported were measured at least 15 minutes after removal from the artery chamber since no significant change in artery length (>0.1 mm) was seen after this time.

Wall thickness: Increased mean intravascular pressure (i.e., hypertension) results in remodeling of blood vessels characterized by increased ratio thickness and alterations in the zero-stress state of the vessel (Fung et al., 1991). In vivo, hypertension results in increased transmural pressure that in turn results in increased radial strain and transmural flow making it difficult to identify which mechanical stimulus is responsible for the observed remodeling. Ex vivo, it is possible to independently control intravascular and extravascular pressure.

To determine whether intravascular pressure was affecting remodeling directly, or whether it was acting by its effect on transmural pressure, porcine carotid arteries were exposed to the three sets of conditions summarized in Table 4. Vessels in the control group were exposed to normal arterial pressures; vessels in the "normal" hypertension group were subjected to elevated intravascular pressure, but a normal extravascular pressure, as is normally the case with hypertension. Both the intravascular and extravascular pressures were increased by an equal amount so that transmural pressure remains normal for vessels in the "corrected" hypertension group. The fact that vessels in the normal hypertension group, but not the other two groups, experience medial thickening was a confirmation that intravascular pressure affects remodeling by its effect on transmural pressure, as opposed to directly.

TABLE 4

A summary of experimental groups.

| Condition | Number of vessels | Intravascular pressure | Extravascular pressure | Transmural pressure |
|---|---|---|---|---|
| 1) Control | 3 | 100/60 | 0 | Normal |
| 2) Normal hypertension | 3 | 200/160 | 0 | Elevated |
| 3) "Corrected" hypertension | 3 | 200/160 | 100 | Normal |

All pressures are in mm of Hg gauge. Flow is pulsatile with ~1 Hz cycle and mean volumetric flow of 300 ml/min.

Internal diameter: To evaluate the hypothesis that chronic changes in luminal diameter resulting from vascular remodeling are also dependent on the wall shear stress, chronic studies were conducted, similar to the acute studies of Melkumyants et al., 1990. The viscosity of the perfusion medium was varied from 1 to 10 cP by the addition of high molecular weight dextran, a compound that is not harmful to excised vessels in chronic cultures (Chesler et al., 1990). Excised porcine carotid arteries were perfused under the conditions described in Table 4. A summary is presented in Table 5 of the experimental groups used to investigate the relative contribution of fluid flow and shear stress on vascular remodeling leading to increases in internal diameter.

TABLE 5

| Condition | Number of vessels | Flow rate (ml/min) | Viscosity (cP) | Initial shear stress(dyn/cm$^2$) |
|---|---|---|---|---|
| 1) Control | 3 | 300 | 5 | Normal |
| 2) High flow/ normal shear | 3 | 1500 | 1 | Normal |
| 3) High flow/ high shear | 3 | 1500 | 5 | 5× normal |
| 4) Normal flow/ high shear | 3 | 300 | 25 | 5× normal |

Po=100 mm Hg for all conditions.

In all conditions, the flow is steady. Therefore, flow can be considered as fully developed laminar flow in a circular conduit of constant cross section where the wall shear stress, $\tau_{rz}$, is calculated as:

$$\tau_{rz} = -4Q\mu/\pi r_i^3$$

The internal diameter of the vessels was assessed throughout the experiment. At the conclusion of the experiment, the arteries were fixed at a pressure of 100 mm Hg and histological sections are prepared. The fact that shear stress regulates chronic changes in lumenal diameter is shown by the finding that groups 1 and 2 have the same diameter as each other, but they have a smaller diameter than that which was found in groups 3 and 4.

Figure 7A:
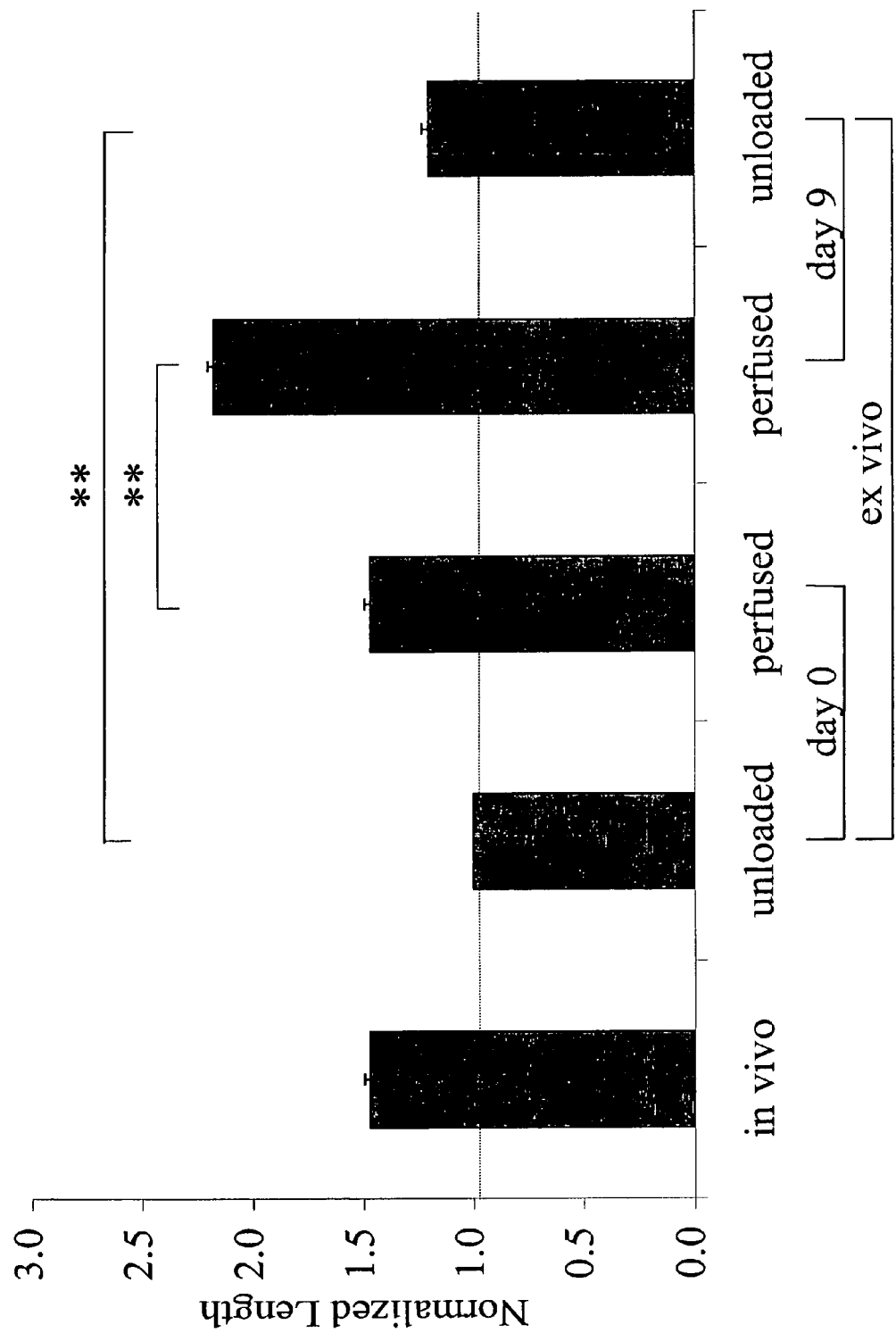
FIGS. 7A and 7B graphically depict artery length for juvenile elongation (n=6, FIG. 7A) and control (n=4, FIG. 7B) experiments. Each artery length was normalized by individual ex vivo unloaded length (i.e., all artery unloaded lengths are 1 on day 0); average data are shown with SEM. Perfused refers to loaded length of the arteries while in the perfusion system, while the unloaded length refers to arteries out of the system, under no load. (**) indicates p<0.005.

Results: The maximum elongation while retaining mechanical integrity and viability was achieved by stretching $\frac{1}{12}^{th}$ of the physiological loaded length (8.3%) on days 2 to 7 of a 9-day experiment. Six arteries were successfully lengthened in the perfusion system 48.1±2.8% from the initial physiological loaded length (p<0.001). The corresponding increase from initial to final ex vivo unloaded length upon removal from the system was 20.5±3.3% (p<0.005)(FIG. 7A).

Figure 7B:
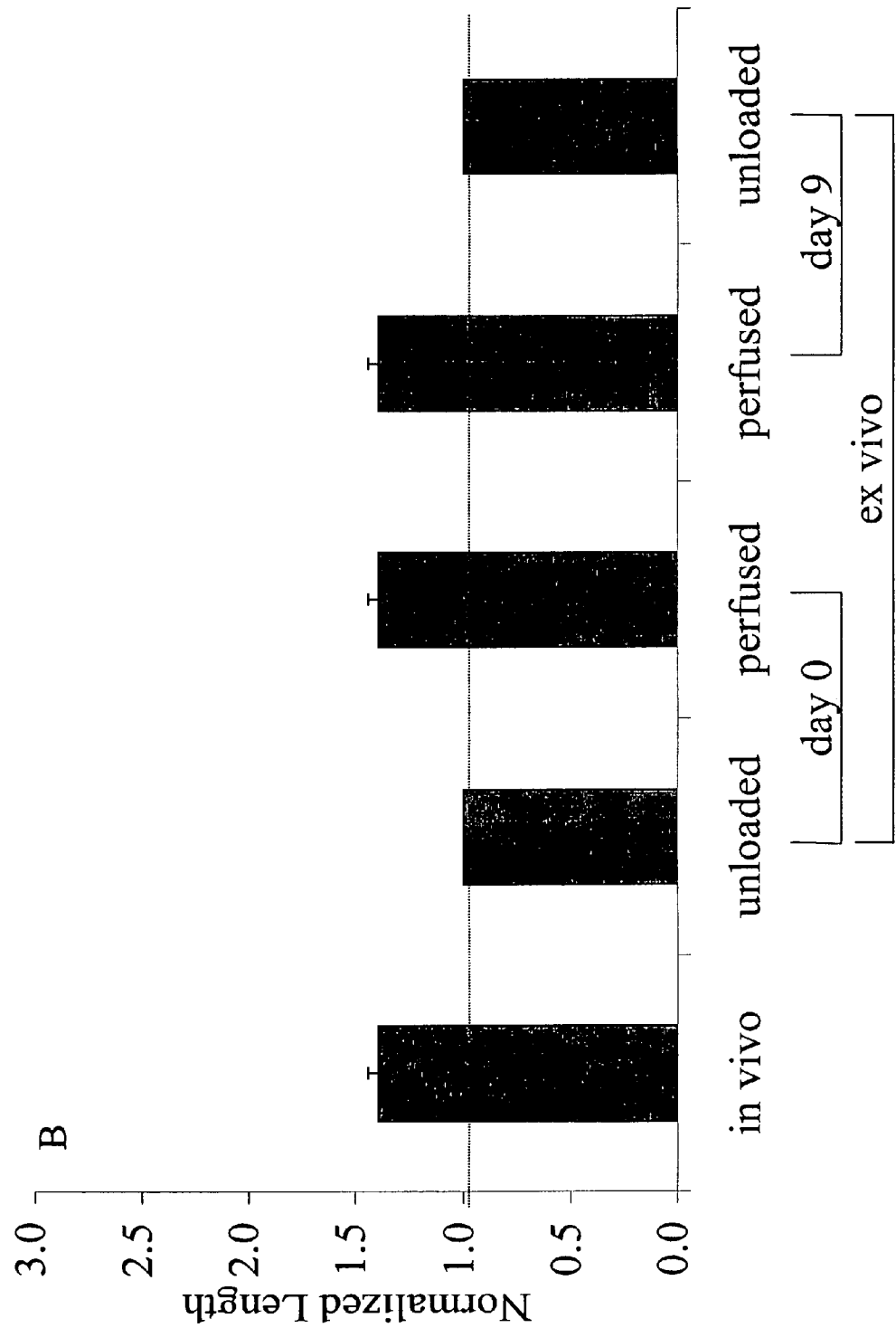

In contrast, none of the six control arteries perfused at physiological loaded length for 9 days (n=6) retained a length increase upon removal from the perfusion system (FIG. 7B).

The wall thickness of control arteries was significantly lower than both elongated (p<0.005) and freshly harvested arteries (p<0.005), whereas the wall thickness of elongated arteries was similar to freshly harvested specimens (Table 6).

TABLE 6

Material properties for juvenile arteries.

| | Freshly Harvested | Elongated | Control |
|---|---|---|---|
| Wall thickness (mm) | 0.80 ± 0.04 (n = 9) | 0.87 ± 0.08 (n = 6) | 0.48 ± 0.02 (n = 5)**,++ |
| Change in wet weight (%) | N/A | 39.9 ± 18.4 (n = 5) | 21.5 ± 2.0 (n = 2) |
| Dry/wet weight (%) | 13.1 ± 0.9 (n = 6) | 12.2 ± 0.4 (n = 4) | 14.7 ± 2.8 (n = 2) |

Data are shown ± standard error of the mean (SEM). Significant differences were found between fresh and control arteries (**), and elongated and control arteries (++), with p<0.005.

As compared to freshly harvested arteries, the wet weight of elongated arteries increased 39.9±18.4% (n=5, p=0.07), whereas the wet weight of control arteries increased 21.5±2.0% (n=2, p=0.06) (Table 6). The dry/wet weight ratio was not significantly different between fresh, control or elongated arteries (Table 6).

Three arteries elongated $\frac{1}{12}^{th}$ of their physiological length on days 2 to 7 were removed before day 9. One was removed from the perfusion system on day 7 (after an elongation of 50%) due to a slow leak, but showed no other problems and was included in the analysis.

More rapid elongation (i.e., >10%/day) always caused arteries from juvenile animals to rupture (Table 3). Three arteries ruptured when elongated $\frac{1}{6}^{th}$ of the physiological loaded length daily (16.7%/day) on days 2, 3 and 5 of 9, while one artery failed on day 3 of 7 when elongated $\frac{1}{8}^{th}$ of the physiological loaded length daily (12.5%/day) on days 2 to 6. None of the arteries that ruptured retained a permanent unloaded length increase upon removal from the system.

Figure 8:
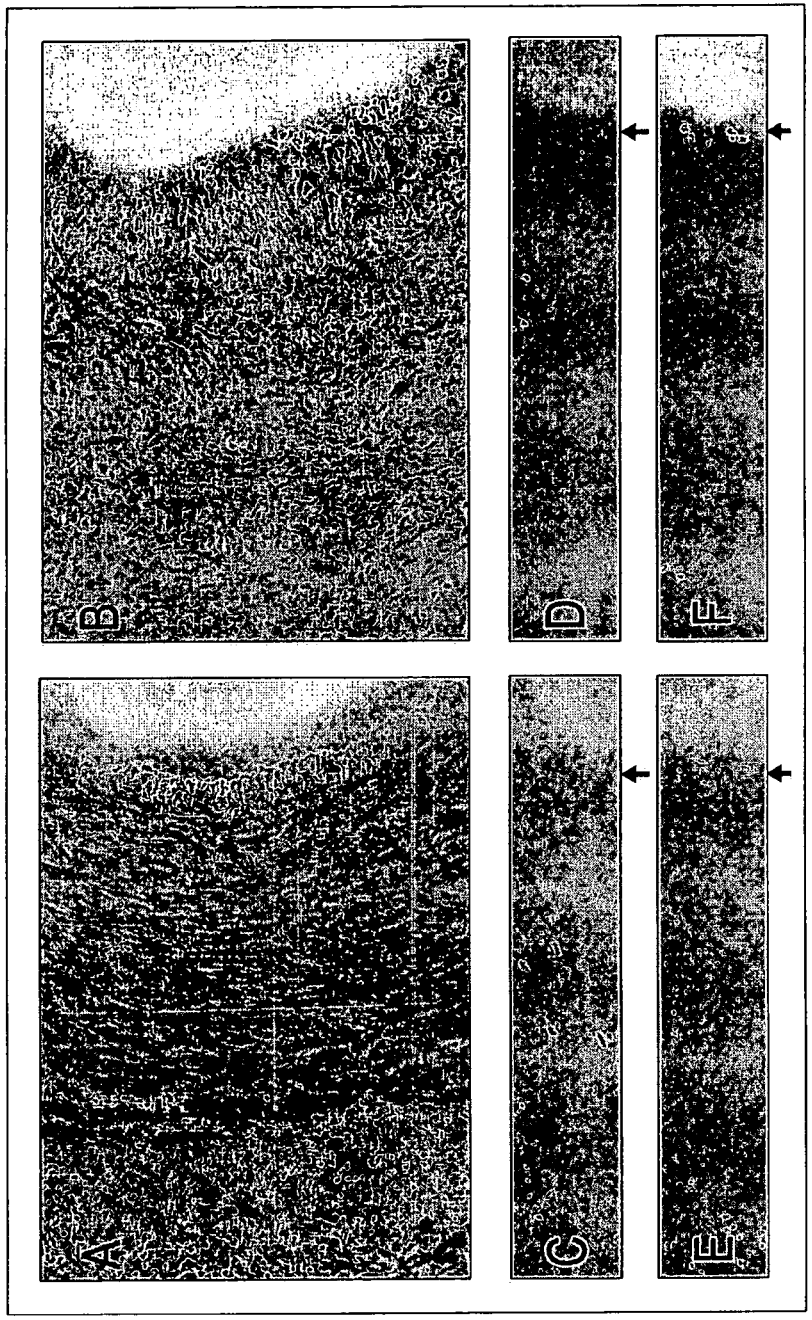
FIGS. 8A–8F provide a comparison of representative histological sections of fresh and elongated arteries from juvenile pigs taken at 10×. Sections were stained with hematoxylin and eosin (H & E, FIGS. 8A and 8B), PCNA (FIGS. 8C and 8D), and the TUNEL assay (FIGS. 8E and 8F). Arrows in FIGS. 8C, 8D, 8E and 8F indicate approximate lumen location (lumen always faces right).

While both elongation of the juvenile vessels in the perfusion system (while under load) and the increased unloaded length indicate arterial elongation, the more relevant parameter is the increase in length at physiological longitudinal stress. Noting that the average physiological longitudinal strain is 50% (bar 1 vs. bar 2 of FIG. 7A), the average physiological longitudinal stress at 50% strain for fresh arteries is 0.40 MPa (mega Pascals)(FIG. 8).

The longitudinal strain of elongated arteries at 0.40 MPa is 72%. Taken together (i.e., the product of the unstressed length and the longitudinal strain at physiological stress), these data indicate that arteries from juvenile pigs elongated for 9 days ex vivo are 40% longer than equivalent fresh arteries at physiological longitudinal stresses. Interestingly, the stress-strain curve for elongated arteries was found to closely resemble the curve for control arteries. Thus, the increase in longitudinal extensibility at relatively low stress appears to be a result of ex vivo culture, rather than the increase in the applied longitudinal stress or strain.

Several non-exclusive mechanisms may contribute to the observed elongation of juvenile arteries including plastic deformation due to the applied longitudinal stress/strain (i.e., creep), mechanically-induced, biologically-mediated redistribution of tissue components (i.e., remodeling without growth), and mechanically-induced, biologically-mediated deposition of new tissue components (i.e., growth). While both creep and remodeling without growth could account for limited lengthening of the arteries, substantial elongation of arteries without substantially decreasing wall thickness or inner diameter would require growth as well. As a result, the 40% increase in wet weight of the arteries as the result of the 9-day elongation process shows that growth is occurring during the elongation of the arteries. Associated with this increase in wet weight, there is a small (1.07-fold) increase in hydration of the arteries, but the majority of increase in wet weight is due to the 29% increase in the dry weight of the elongated arteries.

The greater ability of juvenile arteries to remodel as compared to adult arteries is consistent with data from in vivo studies showing that both adult and juvenile arteries can remodel in response to changes in their mechanical environment, but that juvenile respond more readily. Langille et al., *Am. J. Physiol.* 256:H931–939 (1989); Miyashiro et al., *Circ. Res.* 81:311–319 (1997)). By comparison, neonatal arteries elongated up to 100% under load and 65% when unloaded within 9 days, though as reported by Clerin et al., 2001, even control neonatal arteries had reduced viability over 9 days in culture with physiological flow rates.

Example 3

Control of Extravascular Pressure

Since vessels are compliant viscoelastic materials, adequate control of the extravascular pressure was essential to validate the accuracy of the estimates for transmural pressure. Accordingly, to critically contol extravascular pressure (i.e., the pressure of the medium bathing the external surface of the vessel), pressures were measured by placing a catheter pressure transducer close to the external surface of a segment of compliant Penrose tubing used as a surrogate of an artery for these preliminary studies and compared measured values to the set point values.

A goal of this experiment was to reduce both the magnitude and the variation in the transmural pressure across a compliant tube (e.g., 30±10 mm Hg controlled, as opposed to 120±25 mm Hg uncontrolled). As shown in FIG. 3B, these data indicate that extravascular pressure was accurately controlled to a constant value, and transmural pressure was controlled with a degree of success which appeared to be sufficient to evaluate the relative role of transmural pressure in vascular remodeling.

These findings are adaptable to studies with arteries because when measured pressures are found to vary significantly from predicted values, the measured values were used for subsequent analyses. Therefore, the degree of control of transmural pressure, which was obtained when supplemented with measurements of the intravascular and extravascular pressures, enabled detailed study of the effects of the relative contribution of absolute pressure, transmural pressure, and cyclic strain on vascular remodeling, each of which is an aspect of the mechanical environment affecting vascular cells and blood vessels.

Example 4

Viability, Structure, and Function of Arteries After Ex vivo Culture

Porcine carotid arteries were harvested and cultured in the ex vivo perfusion system under mechanical active environments for up to 9 days as described in Example 2. Vessels were harvested at select times (time zero, 1 hr and 1, 3, 5, and 9 days) and the viability, structure, and function of the vessels were assessed using various criteria summarized in Table 7. The following results compare freshly harvested porcine carotid arteries to vessels perfused ex vivo.

TABLE 7

| Assay | Measure of | Major results/implications |
|---|---|---|
| Viability | | |
| MTT | Mitochondrial activity | Viability not diminished after 9 days in culture |
| PCNA | # of proliferating cells in histological section | Increased cell proliferation through-out full thickness of vessel wall |
| TUNEL | # of cells with fragmented DNA in histological section (indicating apoptosis or necrosis) | Normal levels of apoptosis and necrosis |
| Structure | | |
| H&E | Histological/microscopic structure | General arterial structure preserved; No intimal hyperplasia |
| Elastin | Stains internal elastic lamina (IEL) in histological sections | Internal elastic lamina and elastic layer in media intact |
| Smooth muscle α actin | Stains smooth muscle cells in histological sections | Strong staining in media similar to fresh isolated arteries |
| SEM | Microstructure of luminal surface | Endothelium intact, but with some cells rounded up |
| Function | | |
| Macroscopic Assessment | Occlusion, aneurysms, and "hemorrhage" | Vessels intact and non-occluded |
| Addition of KCl | Vasoactive response of vessel exposed to contractile stimulus indicated by altered pressure drop along vessel | Voltage-gated calcium channels and contractile apparatus functional |

Abbreviations: MTT—3(4,5-dimethylthia-zolyl-2)-2,5-dihenyl tetrazolium bromide; PCNA—proliferating cell nuclear antigen; TUNEL—terminal pUTP nick-end labeling; H&E—hematoxylin and eosin; SEM—scanning electron microscope.

By all criteria employed so far, ex vivo cultured vessels have been shown to be nearly identical to freshly harvested vessels.

Histology and TUNEL Assay: Ring samples (~1 mm in length) were taken from fresh and cultured arteries for TUNEL assays and histological evaluation. Samples were fixed overnight in either 70% ethanol or 10% formalin, dehydrated, embedded in paraffin, and cut into 5 µm thick sections, which were mounted onto glass slides. Slides were deparaffinized and stained with hematoxylin and eosin (H & E), the PC10 antibody recognizing proliferating cell nuclear antigen (PCNA/HRP, DAKO, Carpinteria, Calif.), and the in situ Cell Death Detection kit, POD (TUNEL, Roche Molecular Biochemicals, Indianapolis, Ind.) according to manufacturer's instructions or common protocols.

Mitochondrial activity was assessed using the methylthiazol tetrazolium (MTT) assay (Sigma, St. Louis, Mo.). Artery ring samples approximately 1–2 mm in length were incubated in 0.5 mL of 1 mg/nL MTT solution for 24 hours at 37° C., rinsed with 0.9% saline solution, cut into 2–5 pieces, placed in covered containers containing 5 ml of isopropanol and incubated at room temperature for at least 24 hours. The absorbance of 1 mL of the liquid was measured at 550 nm and normalized by the dry weight of the sample. An MTT index was defined as the final normalized MTT value divided by the initial normalized MTT value. An index value near 1 indicated that mitochondrial activity was similar for fresh and cultured specimens.

Figure 6:
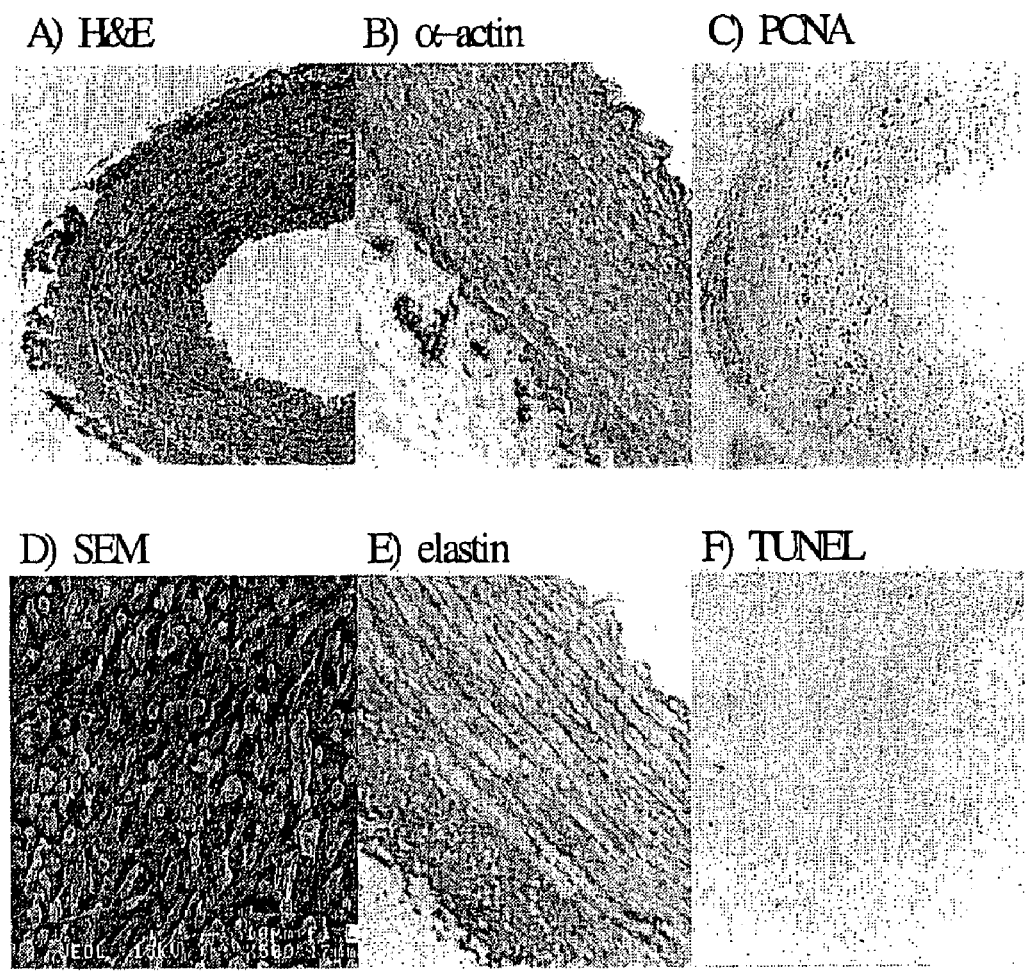
FIGS. 6A–6F photographically depict a microscopic assessment of arteries cultured ex vivo for 9 days under a mechanically active environment.

Viability index measured by MTT was 0.34±0.03 units/mg before perfusion and 0.30±0.08 units/mg after 9 days of perfusion (n=6, p=0.66); the frequency of cells containing fragmented DNA, as measured by the TUNEL assay, were low in both sets of vessel indicating little apoptosis or necrosis (FIG. 5F); and the rate of cell division, indicated by the presence of proliferating cell nuclear antigen (PCNA), was slightly higher in the culture arteries than the freshly harvested arteries (FIG. 5C). The elevated proliferation was not the result of intimal hyperplasia. The gross macroscopic and microscopic structure of the arteries was not changed by ex vivo culture (FIGS. 6A and 6D), nor was the tissue-specific localization of ECM (FIG. 6E) or cells altered (FIG. 6B). Cultured arteries continued to exhibit vasoactive responsiveness (FIG. 6A).

The cellularity, structure, and viability of freshly harvested, control, and successfully (i.e., not ruptured) elongated arteries were similar, as assessed in histological sections stained with H & E (FIGS. 8A and 8B), PCNA (FIGS. 8C and 8D) and TUNEL (FIGS. 8E and 8F). There was no evidence of intimal hyperplasia or fragmentation of the internal elastic lamina in any of the elongated or fresh arteries (FIGS. 8A and 8B). Four of the elongated arteries and five of the control arteries had good endothelial coverage, while two elongated and one control artery were denuded of their endothelial cells. One of the denuded elongated arteries had been denuded (for unknown reasons) prior to installation into the perfusion system, and thus had no endothelial cells after elongation.

TUNEL staining of fresh, elongated and control samples revealed minimal cell death (FIGS. 8E and 8F). An exception to this finding was that the two elongated arteries and one control artery which were denuded of endothelial cells stained strongly for TUNEL, consistent with previous findings that denuded arteries experience progressive cell death beginning in the inner lumen by day 9, irrespective of elongation procedures (Clerin et al., 2001).

Test for Vasoactivity: Vasoactivity experiments were performed on select arteries from juvenile animals upon completion of elongation protocols. Pressure was measured upstream and downstream of the artery in real time to yield the pressure drop caused by the change in arterial inner diameter as endothelial independent vasoactive agents were added to the artery chamber.

Porcine carotid arteries were cultured for 9 days ex vivo. A KCl solution was added to the medium bathing the artery (FIG. 1B) causing the vessel to contract as indicated by the increased average pressure upstream (i.e., an increased pressure drop along the length of the vessel). Though instantaneous pressure fluctuated, as shown in FIG. 2, the time average of the pressure over 1 second is displayed in FIG. 9A. The data represents the response in one vessel, but similar responses were observed in the other vessels investigated.

Vasoconstriction of cultured arteries in response to KCl (FIG. 9A) is a salient observation, because tissue-engineered vessels generated by the methods of L'Heureux et al. and Niklason et al. do not respond to this stimuli (Nicholas L'Heureux, personal communication), indicating that the smooth muscle cells have lost important aspects of their basic function (e.g., their voltage-gated calcium channels), perhaps as the result of their expansion in two-dimensional cell culture prior to their use to form engineered vessels.

Immediately prior to removal from the perfusion system on day 9, three elongated arteries were tested for vasoactive response to norepinephrine (NE) and sodium nitroprusside (SNP), a NO donor. NE was added to the artery chamber to cause vasoconstriction. The arteries were then monitored for roughly 60 minutes, at which time SNP was added to the artery chamber to cause dilation. The pressure drop across the arteries was measured over time to monitor the constriction and dilation caused by these agents.

All arteries tested contracted in response to NE ($1\times10^{-6}$ M (n=2) or $1\times10^{-4}$ M (n=1)), which caused a decrease in lumen diameter corresponding to a peak pressure increase of 52.7±30.3 mm Hg in an average time of 14.8±4.1 minutes. Addition of SNP ($1\times10^{-4}$ M, n=3) caused an increase in lumen diameter corresponding to an average pressure decrease of 38.6±16.0 mm Hg in an average time of 6.8±0.4 minutes.

Evaluation of Mechanical Properties: Samples from select freshly harvested and cultured arteries were evaluated for mechanical properties as follows. Arterial sections approximately 1–2 cm in length were transported in room temperature medium and cut into sheets by one longitudinal incision. Throughout all mechanical evaluation, the specimens were kept at room temperature and constantly hydrated with calcium-free phosphate buffered saline (PBS). The thickness of the specimen was measured at 3 locations using a near frictionless LVDT probe and platform apparatus, after the probe was allowed to reach an equilibrium value (60 seconds).

A "dogbone" stamp was used to cut out a representative sample from the sheet aligned in the longitudinal direction and, when sufficient tissue was available, the circumferential direction. The original test section width was measured with digital calipers. The wide flaps of the samples were wrapped in 400 grit sandpaper and loaded into the tensile testing apparatus (Instron 5543, Canton, Mass.) via spring-loaded grips.

Application of the testing protocol and acquisition of test data were achieved using Instron's Merlin software. The testing consisted of a slow ramp at 0.1 mm/sec, 10 precycles from 0.10 to 0.15 N, a 2-minute hold at constant length, then strain to failure at 0.5 mm/sec. Engineering stress (load/initial cross-sectional area), and engineering strain ((final−initial length)/initial length) were used to determine the stress-strain relationship. Ultimate stress and ultimate strain were defined as the stress or strain at the point when the sample failed.

Figure 10:
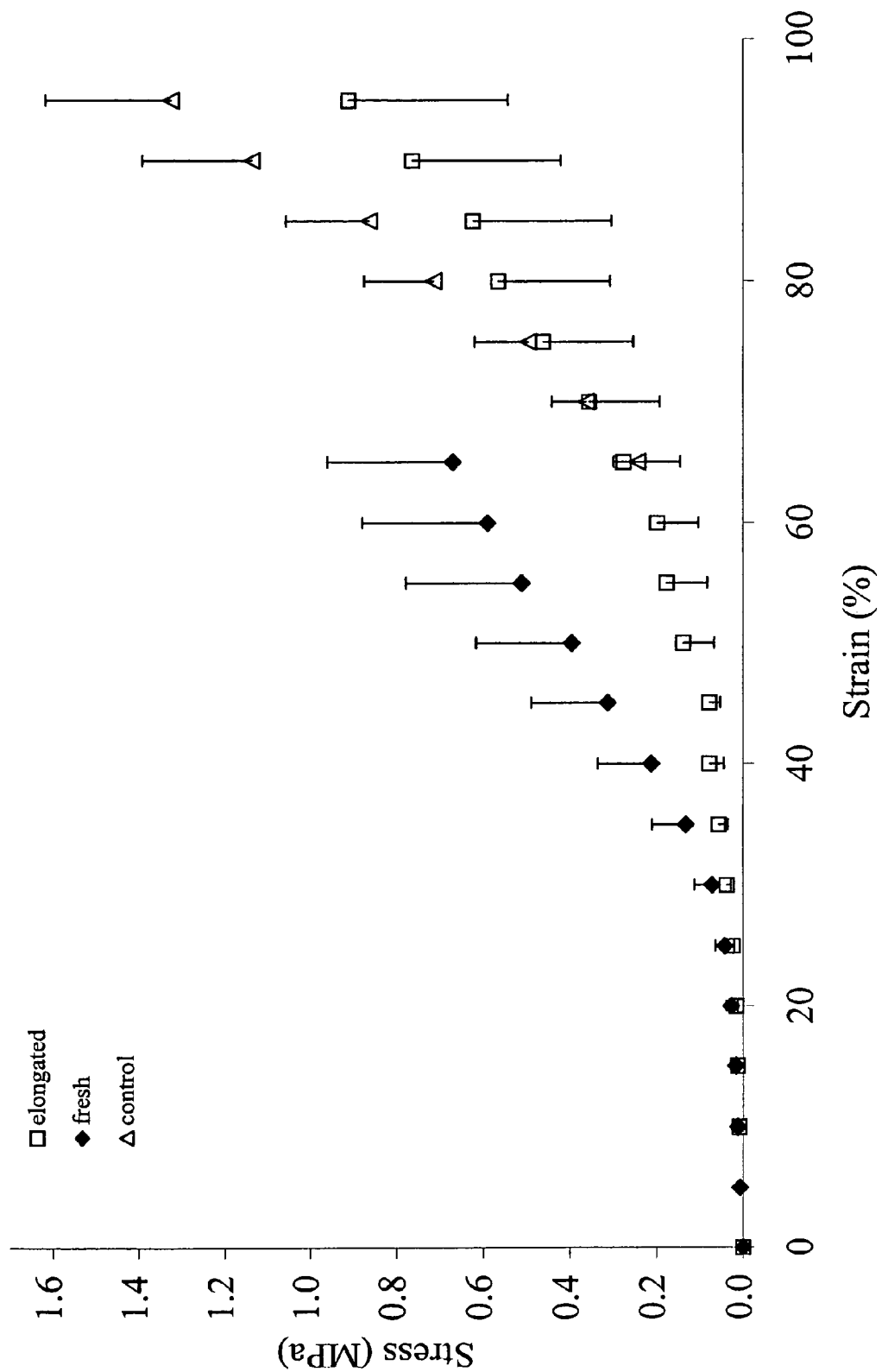
FIG. 10 graphically depicts the average longitudinal stress-strain relationship for fresh (n=9), elongated (n=4), and control (n=5) arteries from juvenile pigs. Data are shown until the first point of failure for each group (e.g., the minimum ultimate strain from the fresh group was 65%). Data were unavailable below 65% for control arteries.

The average stress-strain relations for freshly harvested, elongated, and control arteries are displayed in FIG. 10. Defining the transition zone as the nonlinear region separating two approximately linear regions of different slopes, the transition zone for both the control and elongated arteries ended at about 65% strain, whereas freshly harvested arteries ended at about 35% strain. The average ultimate stress and strain in the longitudinal direction was calculated for fresh, control and elongated arteries; only the ultimate stress of control arteries was significantly different than elongated and freshly harvested arteries (Table 8). The ultimate stress and strain in the circumferential direction were obtained for some fresh and elongated arteries (Table 8).

TABLE 8

Mechanical properties for arteries from juvenile donors.

| | Freshly harvested arteries | Cultured elongated arteries | Cultured control arteries |
|---|---|---|---|
| Longitudinal | (n = 9) | (n = 4) | (n = 5) |
| Ultimate stress (MPa) | 1.41 ± 0.13 | 1.39 ± 0.21 | 2.11 ± 0.10*,## |
| Ultimate strain (%) | 94.1 ± 7.67 | 121 ± 12.9 | 115 ± 9.53 |
| Circumferential | (n = 3) | (n = 4) | |
| Ultimate stress (MPa) | 1.98 ± 0.46 | 0.87 ± 0.09 | N.A. |
| Ultimate strain (%) | 106 ± 3.70 | 89.9 ± 23.6 | N.A. |

Data were determined from mechanical testing in the axial and circumferential directions. Data are shown with the standard error of the means (SEM). Significance differences were denoted between fresh and control arteries (*), and elongated and control arteries (+). One symbol equals $p<0.05$, two equals $p<0.005$. N.A. indicates not analyzed.

Tests for Statistical Significance: In cases when the same specimen could be tracked (such as the artery length before and after culture), one-tailed, paired t-tests were used. Otherwise, one-tailed, two-sample t-tests assuming unequal variance were utilized, $p<0.05$ was considered significant. For figures and tables, one symbol (*) denotes $p<0.05$, while two symbols (**) denote $p<0.005$. The ultimate stress and strain in the circumferential direction were obtained from fresh and elongated arteries (Table 8). While the ultimate circumferential stress of control arteries was 2.3 fold. greater than that of elongated arteries, the difference was not significant ($p=0.07$). Taken together, these data indicate that ex vivo cultured vessels retained their viability, structure and function.

Example 5

Ex vivo Vascular Remodeling

Of the three aspects of arterial remodeling to be investigated (wall thickness, longitudinal length, and internal diameter), the least is known from in vivo studies about the mechanical factors that regulate the longitudinal length of a vessel. Therefore, to test whether longitudinal stress or strain stimulates vessels to elongate, and to further validate the ex vivo perfusion system, four excised porcine carotid arteries were placed in the ex vivo system and initially stretched to their in vivo length. Each day the vessels were stretched an additional ~10% by sliding the stainless steel tubes shown in FIG. 2A. After 9 days in culture, the length of the vessel had increased 100%. In contrast, acute stretching of the arteries resulted in rupture after about 80% strain (FIG. 98B).

Figure 11:
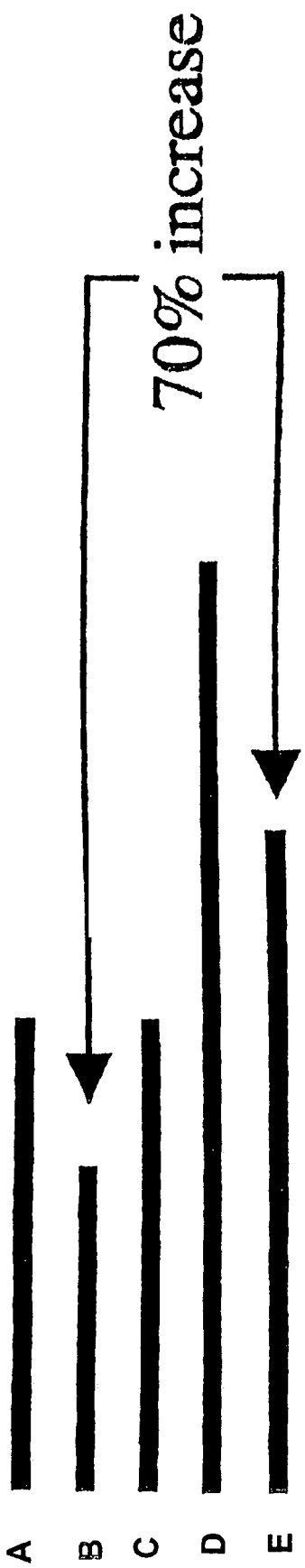
FIG. 11 is a comparative line graph depicting the effect of ex vivo remodeling on the longitudinal length of a vessel after 9 days. The length of the vessel shown by line A (the in vivo length) was equal to that in line C (the initial length in the system). Line B shows the freshly excised length showing elastic recoil from the in vivo length. Line D was the length of the vessel after 9 days in the ex vivo system (showing a 100% increase over the in vivo length. Line E shows the length of the vessel after removal from the ex vivo system, which even after recoil was 70±3% greater than the initial length. The length of line D=2.0× that of line C. The length of line E=1.7× that of line B. Conditions B and E are unstressed (i.e., no applied longitudinal loads); while all other conditions involve longitudinal loading.

When removed from the system, arteries that had been stretched for 9 days shortened (elastic recoil similar to what was observed when vessels were initially excised from in vivo), but the resulting length was 70±3% greater than the initial length of the freshly isolated arteries prior to stretching, as summarized in FIG. 11. The length of the vessel in line A (the in vivo length) was equal to that in line C (the initial length in the system). Line B shows the freshly excised length showing elastic recoil from the in vivo length. Line D was the length of the vessel after 9 days in the ex vivo system (showing a 100% increase over the in vivo length). Line E shows the length of the vessel after removal from the ex vivo system, which even after recoil was 70±3% greater than the initial length. The length in line D=2.0× that of line C. The length in line E=1.7× that of line B. Conditions B and E are unstressed (i.e., no applied longitudinal loads); while all other conditions involve longitudinal loading These data provide evidence that aspects of mechanically induced vascular remodeling observed in vivo can be reproduced in the ex vivo perfusion system of the invention.

Example 6

Evaluating Performance of Tissue-Engineered Blood Vessels In Vivo

To rigorously evaluate the potential utility of ex vivo remodeled arteries for bypass surgery, in vivo studies are being conducted. Ex vivo cultured arteries are implanted as autologous interposition left carotid artery grafts. The in vivo performance of these grafts with respect to patency and resistance to intimal hyperplasia are compared to autologous saphenous vein grafts placed interpositionally in the right carotid arteries of the same test pigs, and freshly harvested carotid arteries (i.e., no ex vivo culture) placed back in their original donor set. This experimental design allows comparison of the ex vivo remodeled vessels to a positive control (the freshly harvested carotid artery, which is an excellent vascular graft material) and a negative control (the saphenous vein, which is a relatively poor vascular graft material).

Several sets of in vivo studies are conducted, wherein the major difference between the two sets being the conditioning of the ex vivo remodeled vessels. The first set of studies is designed to test the hypothesis that ex vivo culture of vessels under mechanical conditions simulating normal physiological loading will result in minimal vascular remodeling, and that the patency of these arteries is approximate that of freshly harvested vessels. In subsequent sets of experiments, the mechanical environment during ex vivo culture is modified to direct the remodeling of the excised vessels.

Example 7

Using the Ex Vivo Perfusion System to Explore the Molecular Regulation of Mechanically Induced Vascular Remodeling To evaluate the expression of Tenascin-C (TN-C) protein and mRNA in arteries exposed to the different mechanical regimes of the present invention, segments of arteries cultured ex vivo are routinely fixed and sectioned to prepare histological sections. Histological sections are immunostained for TN-C protein following a procedure similar to the one used to stain for smooth muscle cell α-actin and PCNA (FIGS. 6B, 6E).

The majority of studies show that soluble, extracellular, and matrix factors regulate TN-C at the transcriptional level, therefore, in situ hybridization studies with digoxigenin-labeled TN-C riboprobes are used to ascertain the regulation of TN-C expression at the mRNA level. If mechanically induced changes in TN-C protein levels in the arterial wall are regulated on the mRNA level, the region(s) of the promoter responsible for mechano-sensitivity are determined using full length and a series of 11 mutated TN-C promoters linked to a CAT reporter gene. These constructs have been previously used to determine to the regions of the TN-C promoter that regulate TN-C transcription by cultured smooth muscle cells in response to remodeled type-I collagen (Jones et al., J. Cell Sci. 112(Pt 4):435–445 (1999)).

The TN-C promoter—CAT reporter plasmids are individually incorporated into a polylactic acid (PLA) (3 mg PLA/1000 ml chloroform) to give a final DNA concentration of 14 μg/ml. DNA-polymer emulsions are applied to the surface of a Dacron mesh, and then desiccated under a laminar flow hood. Plasmid DNA is delivered from an adventitial position by wrapping meshes around isolated arteries prior to their placement in the ex vivo organ culture system. Jones and others have used this technique to deliver DNA to the arterial wall in vivo.

After a period of ex vivo culture exposed to the desired mechanical environment, the artery is retrieved, and a segment of the vessel is fixed in paraformaldehyde, sectioned and immunostained with antibodies that recognize the CAT protein. The remaining segment of the vessel is analyzed for CAT activity using established techniques. By coupling immunostaining of histological sections and quantification of CAT enzyme activity, the spatial distribution and amount of the reporter protein is determined. By comparing the CAT expression driven by different promoters, the salient region(s) for mechanosensitivity are indicated. Special attention is given to the potential role of a putative shear stress responsive element (GAGACC) 600 base pairs upstream from the transcriptional start site.

In sum, the controlled, ex vivo vascular remodeling system and method of the present invention has been shown to provide a clinically significant tool for the tissue engineering of vascular grafts from small excised vessels, as demonstrated at the physical and molecular levels, and as optimized in vivo. Consistent with the principle that tissue-engineered arteries generated by the present invention more closely resemble the structure and function of native arteries than arteries constructed from isolated cells, arteries isolated from juvenile pigs and elongated ex vivo were nearly identical to native arteries in terms of structure (both macroscopically and histologically, including endothelial coverage and intricate structural components such as the internal elastic lamina), viability (as measured with the MTT assay and TUNEL analysis), and function (vasoactivity and mechanical properties). Aside from increased extensibility at low stress, the biomechanical properties of fresh and elongated arteries, notably the ultimate longitudinal and circumferential stresses and strains, were not significantly different from fresh arteries demonstrating that when the elongated arteries are used as vascular grafts, they are expected to behave in a manner similar to native arteries in terms of mechanical integrity, as well as to provide clinically relevant patency rates when implanted in vivo. Moreover, ex vivo it is possible to precisely control the mechanical environment while carefully monitoring the resulting growth/remodeling, thereby opening new avenues of research regarding the mechanical stimuli responsible for specific aspects of remodeling in vivo.

Each and every patent, patent application and publication that is cited in the foregoing specification is herein incorporated by reference in its entirety.

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the spirit and scope of the invention. Such modifications, equivalent variations and additional embodiments are also intended to fall within the scope of the appended claims.

What is claimed is:

1. A method of physically remodeling and tissue engineering a small blood vessel, while maintaining the viability of the vessel, comprising the steps of:
   excising the blood vessel from its native site, and
   subjecting the excised vessel to a precisely controlled, and real-time monitored, ex vivo mechanical environment for a time sufficient to remodel the vessel by increasing the diameter, length, or wall thickness of the vessel, or any combination thereof.

2. The method of claim 1, wherein the excised vessel is a small artery or a vein.

3. The method of claim 1, further comprising applying pressure, shear, and strain to the vessel under controlled conditions within the mechanical environment, wherein transmural pressure drop regulates wall thickness, longitudinal tension regulates length, and flow-induced shear stress regulates inner diameter of the remodeled vessel.

4. The method of claim 3, further comprising controlling the mechanical environment by an ex vivo perfusion system, and supplying the mechanical environment with a traditional cell or organ culture system, thereby providing regulated temperature, $pO_2$, $pCO_2$ and nutrients.

5. The method of claim 1, wherein length of the remodeled vessel is increased at least 100% over its native length when excised, and wherein more than 50% of the increased length is retained after recoil when the remodeled vessel is removed from the controlled mechanical environment.

6. A method of physically remodeling a small blood vessel to be used in vivo as a vascular graft in a patient in need of such a graft, comprising the steps of:
   excising the blood vessel from its native site; and
   subjecting the excised vessel to a controlled, real-time monitored, ex vivo mechanical environment for a time sufficient to increase diameter, length, or wall thickness of the vessel, or any combination thereof;
   removing the remodeled vessel from the ex vivo mechanical environment; and
   surgically inserting the remodeled vessel in vivo as a vascular graft (artery or vein) into the patient.

7. The method of claim 6, wherein the excised vessel is a small artery or a vein.

8. The method of claim 6, wherein the excised vessel is autologous to the patient.

9. The method of claim 6, further comprising applying pressure, shear, and strain to the vessel under controlled conditions within the mechanical environment, wherein transmural pressure drop regulates wall thickness, longitudinal tension regulates length, and flow-induced shear stress regulates inner diameter of the remodeled vessel.

10. The method of claim 6, further comprising controlling the mechanical environment is controlled by an ex vivo perfusion system, and supplying the mechanical environment with a traditional cell or organ culture system, thereby providing regulated temperature, $pO_2$, $pCO_2$ and nutrients.

11. The method of claim 6, wherein length of the remodeled vessel is increased at least 100% over its native length when excised, and wherein more than 50% of the increased length is retained after recoil when the remodeled vessel is removed from the controlled mechanical environment.

12. An ex vivo perfusion system for exposing one or more viable, excised, small blood vessels, which is/are arterial or venous, to precisely controlled flow and pressure regimes, wherein the system comprises:
   a pump means, which when activated, continuously pushes fluid through the system;
   a housing means, comprising a medium-filled chamber, within which chamber the excised vessel is housed, and the excised vessel is cannulated with two sliding tubes that can be moved apart in a controlled manner to expand the length of the vessel, wherein when activated, the chamber housing the vessel is perfused with cell culture medium supplemented with serum and antibiotics, and wherein temperature, pH, $pO_2$, $pCO_2$, and nutrients are maintained at levels sufficient to maintain the viability of the vessel;
   a reservoir within which the culture medium is pooled, having a gas exchange port, which permits gas exchange within the medium;
   a controller means to control pressure within the chamber housing the excised blood vessel;
   an in-line probe means to measure and report pressure within the system;
   a data measurement means attached to the in-line probe means for digitizingthe measured pressure data; and
   a computer node attached to the data measurement means to record, analyze and store the digital data.

13. The ex vivo perfusion system of claim 12, wherein the system further comprises:
   as the pump means, a pulsatile blood pump, which when activated, continuously pushes fluid through the system;
   as the housing means, an enclosed Plexiglas cylinder, which forms the housing comprising a medium-filled chamber, cannulated on each end, within which chamber the excised vessel is cannulated with two sliding stainless-steel tubes, wherein the chamber housing the vessel is perfused with cell culture medium supplemented with serum and antibiotics, and wherein temperature, pH, $pO_2$, $pCO_2$, and nutrients are maintained at levels sufficient to maintain the viability of the vessel;
   a reservoir within which the culture medium is pooled, having a gas exchange port, which permits gas exchange within the medium, before the medium is returned to the pump for circulation within the system;
   as a controller, a needle valve controller at either end of the chamber to control pressure within the chamber housing the excised blood vessel;
   as an in-line probe, at least one in-line probe to measure pressure within the system at a rate of approximately 250 times per second, wherein the data is reported in analog;
   as a data measurement means, a data measurement module attached to the in-line probe(s) for digitizing the analog pressure.

14. The system of claim 12, wherein when multiple excised small blood vessels are exposed to precisely controlled flow and pressure regimes, the vessels are run in parallel, wherein each vessel is contained within its own housing, having corresponding chambers and needle valves.

15. The system of claim 12, wherein ports on the Plexiglas cylinder allow the exchange of medium and nutrients, fluid overflow and air/$CO_2$ discharge.

16. The system of claim 12, wherein improved control of the mechanical environment provides localized intravascular and extravascular pressure measurement and control, providing real time monitoring of vessel remodeling.

17. The system of claim 13, wherein the two sliding stainless-steel tubes slide independently of the rest of the unit to control vessel strain.

18. A method of physically remodeling an excised small blood vessel, said method comprising
   cannulating each end of the excised vessel to two sliding stainless-steel tubes that are cannulated on each end and that are contained within an enclosed medium-filled chamber,
   gradually extending the vessel without rupture by slowly extending the stainless steel tubes on which the vessel is mounted within the enclosed media filled chamber, while
   maintaining the viability of the vessel by perfusing the vessel under precisely controlled flow and pressure regimes with cell culture medium supplemented with serum and antibiotics, and wherein temperature, pH, $pO_2$, $pCO_2$, and nutrients are maintained at levels sufficient to maintain the viability of the vessel.

* * * * *